United States Patent
Dehaspe et al.

(10) Patent No.: US 11,535,896 B2
(45) Date of Patent: Dec. 27, 2022

(54) METHOD FOR ANALYSING CELL-FREE NUCLEIC ACIDS

(71) Applicant: Katholieke Universiteit Leuven, Leuven (BE)

(72) Inventors: Luc Dehaspe, Heverlee (BE); Joris Vermeesch, Veltem (BE)

(73) Assignee: Katholieke Universiteit Leuven, Leuven (BE)

( * ) Notice: Subject to any disclaimer, the term of this patent is extended or adjusted under 35 U.S.C. 154(b) by 623 days.

(21) Appl. No.: 16/613,991

(22) PCT Filed: May 15, 2018

(86) PCT No.: PCT/EP2018/062615
§ 371 (c)(1),
(2) Date: Nov. 15, 2019

(87) PCT Pub. No.: WO2018/210877
PCT Pub. Date: Nov. 22, 2018

(65) Prior Publication Data
US 2020/0080158 A1    Mar. 12, 2020

(30) Foreign Application Priority Data

May 15, 2017 (GB) ..................................... 1707735
May 23, 2017 (LU) .................................. LU100253

(51) Int. Cl.
| | |
|---|---|
| *C12Q 1/6886* | (2018.01) |
| *G16H 50/30* | (2018.01) |
| *G16H 50/20* | (2018.01) |
| *G16B 20/20* | (2019.01) |
| *G16B 40/10* | (2019.01) |

(Continued)

(52) U.S. Cl.
CPC ......... *C12Q 1/6886* (2013.01); *C12Q 1/6827* (2013.01); *C12Q 1/6869* (2013.01); *G16B 20/20* (2019.02); *G16B 40/10* (2019.02); *G16B 40/20* (2019.02); *G16H 50/20* (2018.01); *G16H 50/30* (2018.01); *C12Q 2600/158* (2013.01)

(58) Field of Classification Search
CPC ..................................................... G16B 40/20
See application file for complete search history.

(56) References Cited

U.S. PATENT DOCUMENTS

2018/0082012 A1 * 3/2018 Jiang ...................... G16B 20/10

FOREIGN PATENT DOCUMENTS

| WO | 2016015058 A2 | 7/2015 |
| WO | 2016094853 A1 | 12/2015 |
| WO | 2016112850 A1 | 1/2016 |

OTHER PUBLICATIONS

European Patent Office Search Report in reference to co-pending European Patent Application No. PCT/EP2018/062615 filed May 15, 2018.

(Continued)

*Primary Examiner* — Edward Park
(74) *Attorney, Agent, or Firm* — Dinsmore & Shohl LLP

(57) ABSTRACT

The present invention concerns the analysis of cell-free nucleic acids to determine the contribution of cell-free nucleic acids from specific tissues. In addition, the invention provides methods for diagnosing diseases based on cell-free nucleic acid analysis. The methods of the invention are also useful to detect quality defects in samples containing cell-free nucleic acids.

8 Claims, 33 Drawing Sheets

| | | STATS A | | | STATS B | | | STATS B/A | |
|---|---|---|---|---|---|---|---|---|---|
| | | | Normalization | | | Normalization | | Normalization | |
| Bin | Count | SUM=1 | MED=1 | Count | SUM=1 | MED=1 | SUM=1 | MED=1 |
| 1 | 119 | 0.09 | 0.87 | 1498 | 0.54 | 10.23 | 6.29 | 11.77 |
| 2 | 186 | 0.13 | 1.36 | 186 | 0.07 | 1.27 | 0.50 | 0.94 |
| 3 | 153 | 0.11 | 1.12 | 153 | 0.06 | 1.04 | 0.50 | 0.94 |
| 4 | 120 | 0.09 | 0.88 | 120 | 0.04 | 0.82 | 0.50 | 0.94 |
| 5 | 129 | 0.09 | 0.94 | 129 | 0.05 | 0.88 | 0.50 | 0.94 |
| 6 | 100 | 0.07 | 0.73 | 100 | 0.04 | 0.68 | 0.50 | 0.94 |
| 7 | 148 | 0.11 | 1.08 | 148 | 0.05 | 1.01 | 0.50 | 0.94 |
| 8 | 104 | 0.08 | 0.76 | 104 | 0.04 | 0.71 | 0.50 | 0.94 |
| 9 | 175 | 0.13 | 1.28 | 175 | 0.06 | 1.19 | 0.50 | 0.94 |
| 10 | 145 | 0.11 | 1.06 | 145 | 0.05 | 0.99 | 0.50 | 0.94 |

(51) Int. Cl.
      G16B 40/20      (2019.01)
      C12Q 1/6827    (2018.01)
      C12Q 1/6869    (2018.01)

(56) References Cited

OTHER PUBLICATIONS

Chen, et al., "Noninvasive Prenatal Diagnosis of Fetal Trisomy 18 and Trisomy 13 by Maternal plasma DNA Sequencing", PLOS One, vol. 6, Issue 7, pp. 1-7, Jul. 2011.

Van Roy, et al., "Shallow Whole Genome Sequencing on Circulating Cell-Free DNA Allows Reliable Noninvasive Copy-Number Profiling in Neuroblastoma Patients", Clinical Cancer Research, vol. 23, No. 20, Jul. 14, 2017, pp. 6305-6314, XP055441158.

Kirkizlar, et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 1, 2015, pp. 407-116, XP055441218.

Snyder, et al., "Cell-free DNA comprises an in vivo nucleosome footprint that informs its tissues-of-origin", HHS Public Access, pp. 1-24, Jan. 14, 2016.

* cited by examiner

|  | STATS A | | | STATS B | | | STATS B/A | |
|---|---|---|---|---|---|---|---|---|
|  |  | Normalization | | | Normalization | | Normalization | |
| Bin | Count | SUM=1 | MED=1 | Count | SUM=1 | MED=1 | SUM=1 | MED=1 |
| 1 | 119 | 0.09 | 0.87 | 1498 | 0.54 | 10.23 | 6.29 | 11.77 |
| 2 | 186 | 0.13 | 1.36 | 186 | 0.07 | 1.27 | 0.50 | 0.94 |
| 3 | 153 | 0.11 | 1.12 | 153 | 0.06 | 1.04 | 0.50 | 0.94 |
| 4 | 120 | 0.09 | 0.88 | 120 | 0.04 | 0.82 | 0.50 | 0.94 |
| 5 | 129 | 0.09 | 0.94 | 129 | 0.05 | 0.88 | 0.50 | 0.94 |
| 6 | 100 | 0.07 | 0.73 | 100 | 0.04 | 0.68 | 0.50 | 0.94 |
| 7 | 148 | 0.11 | 1.08 | 148 | 0.05 | 1.01 | 0.50 | 0.94 |
| 8 | 104 | 0.08 | 0.76 | 104 | 0.04 | 0.71 | 0.50 | 0.94 |
| 9 | 175 | 0.13 | 1.28 | 175 | 0.06 | 1.19 | 0.50 | 0.94 |
| 10 | 145 | 0.11 | 1.06 | 145 | 0.05 | 0.99 | 0.50 | 0.94 |

Figure 1

| Bin | 1 | 2 | 3 | 4 | 5 | 6 | 7 | 8 | 9 | 10 |
|---|---|---|---|---|---|---|---|---|---|---|
| Normalized bin count Sample 1 | 0.66 | 1.19 | 0.67 | 1.07 | 0.8 | 1.27 | 1.2 | 0.71 | 1.19 | 0.86 |
| Normalized bin count Sample 2 | 0.94 | 0.74 | 0.81 | 0.80 | 1.06 | 1.15 | 0.70 | 1.12 | 1.14 | 1.32 |
|  | 0.66 | 1.19 |  |  |  |  |  |  |  |  |
|  | 0.94 | 0.74 |  |  |  |  |  |  |  |  |
|  | 0.88 |  |  |  |  |  |  |  |  |  |
|  | 0.66 | 1.19 | 0.67 |  |  |  |  |  |  |  |
|  | 0.94 | 0.74 | 0.81 |  |  |  |  |  |  |  |
|  |  | 0.84 |  |  |  |  |  |  |  |  |
|  |  | 1.19 | 0.67 | 1.07 |  |  |  |  |  |  |
|  |  | 0.74 | 0.81 | 0.80 |  |  |  |  |  |  |
|  |  |  | 0.88 |  |  |  |  |  |  |  |
|  |  |  | 0.67 | 1.07 | 0.80 |  |  |  |  |  |
|  |  |  | 0.81 | 0.80 | 1.06 |  |  |  |  |  |
|  |  |  |  | 0.87 |  |  |  |  |  |  |
|  |  |  |  | 1.07 | 0.80 | 1.27 |  |  |  |  |
|  |  |  |  | 0.80 | 1.06 | 1.15 |  |  |  |  |
|  |  |  |  |  | 1.02 |  |  |  |  |  |
|  |  |  |  |  | 0.80 | 1.27 | 1.20 |  |  |  |
|  |  |  |  |  | 1.06 | 1.15 | 0.70 |  |  |  |
|  |  |  |  |  |  | 1.03 |  |  |  |  |
|  |  |  |  |  |  | 1.27 | 1.20 | 0.71 |  |  |
|  |  |  |  |  |  | 1.15 | 0.70 | 1.12 |  |  |
|  |  |  |  |  |  |  | 1.03 |  |  |  |
|  |  |  |  |  |  |  | 1.20 | 0.71 | 1.19 |  |
|  |  |  |  |  |  |  | 0.70 | 1.12 | 1.14 |  |
|  |  |  |  |  |  |  |  | 1.01 |  |  |
|  |  |  |  |  |  |  |  | 0.71 | 1.19 | 0.86 |
|  |  |  |  |  |  |  |  | 1.12 | 1.14 | 1.32 |
|  |  |  |  |  |  |  |  |  | 1.06 |  |
|  |  |  |  |  |  |  |  |  | 1.19 | 0.86 |
|  |  |  |  |  |  |  |  |  | 1.14 | 1.32 |
|  |  |  |  |  |  |  |  |  |  | 1.13 |
| GipSeq-count mean | 0.88 | 0.84 | 0.88 | 0.87 | 1.02 | 1.03 | 1.03 | 1.01 | 1.06 | 1.13 |
| *Reference GipSeq-count mean* | *0.72* | *1.06* | *0.91* | *0.95* | *0.8* | *1.22* | *1.02* | *0.97* | *1.02* | *1.12* |
| *Reference GipSeq-count SD* | *0.02* | *0.07* | *0.07* | *0.03* | *0.07* | *0.09* | *0.1* | *0.03* | *0.05* | *0.04* |
| GipSeq-count-Z-profile | 5.57 | -2.16 | -0.28 | -1.86 | 2.17 | -1.43 | 0.04 | 0.90 | 0.48 | 0.11 |
| GipSeq-count-L2R-profile | 0.30 | -0.34 | -0.05 | -0.13 | 0.36 | -0.24 | 0.01 | 0.06 | 0.05 | 0.01 |
| GipSeq-count-P-profile | 0.50 | -0.67 | -0.33 | -0.33 | 1.00 | -0.67 | 0.33 | 0.33 | 0.33 | 0.50 |
| Sign-count | + | - | - | - | + | - | + | + | + | + |
| GipSeq-count-S-profile |  |  |  |  |  |  |  |  |  |  |

Figure 3

| Bin | 1 | 2 | 3 | 4 | 5 | 6 | 7 | 8 | 9 | 10 |
|---|---|---|---|---|---|---|---|---|---|---|
| 1000 * Mutation burden Sample 1 | 0.90 | 0.95 | 1.45 | 1.10 | 1.97 | 1.20 | 1.26 | 1.36 | 1.42 | 1.41 |
| 1000 * Mutation burden Sample 2 | 1.40 | 0.80 | 1.56 | 1.04 | 1.62 | 1.19 | 1.76 | 1.49 | 1.03 | 1.11 |
|  | 0.90 | 0.95 |  |  |  |  |  |  |  |  |
|  | 1.40 | 0.80 |  |  |  |  |  |  |  |  |
|  | 1.01 |  |  |  |  |  |  |  |  |  |
|  | 0.90 | 0.95 | 1.45 |  |  |  |  |  |  |  |
|  | 1.40 | 0.80 | 1.56 |  |  |  |  |  |  |  |
|  |  | 1.18 |  |  |  |  |  |  |  |  |
|  |  | 0.95 | 1.45 | 1.10 |  |  |  |  |  |  |
|  |  | 0.80 | 1.56 | 1.04 |  |  |  |  |  |  |
|  |  |  | 1.15 |  |  |  |  |  |  |  |
|  |  |  | 1.45 | 1.10 | 1.97 |  |  |  |  |  |
|  |  |  | 1.56 | 1.04 | 1.62 |  |  |  |  |  |
|  |  |  |  | 1.45 |  |  |  |  |  |  |
|  |  |  |  | 1.10 | 1.97 | 1.20 |  |  |  |  |
|  |  |  |  | 1.04 | 1.62 | 1.19 |  |  |  |  |
|  |  |  |  |  | 1.35 |  |  |  |  |  |
|  |  |  |  |  | 1.97 | 1.20 | 1.26 |  |  |  |
|  |  |  |  |  | 1.62 | 1.19 | 1.76 |  |  |  |
|  |  |  |  |  |  | 1.50 |  |  |  |  |
|  |  |  |  |  |  | 1.20 | 1.26 | 1.36 |  |  |
|  |  |  |  |  |  | 1.19 | 1.76 | 1.49 |  |  |
|  |  |  |  |  |  |  | 1.38 |  |  |  |
|  |  |  |  |  |  |  | 1.26 | 1.36 | 1.42 |  |
|  |  |  |  |  |  |  | 1.76 | 1.49 | 1.03 |  |
|  |  |  |  |  |  |  |  | 1.39 |  |  |
|  |  |  |  |  |  |  |  | 1.36 | 1.42 | 1.41 |
|  |  |  |  |  |  |  |  | 1.49 | 1.03 | 1.11 |
|  |  |  |  |  |  |  |  |  | 1.30 |  |
|  |  |  |  |  |  |  |  |  | 1.42 | 1.41 |
|  |  |  |  |  |  |  |  |  | 1.03 | 1.11 |
|  |  |  |  |  |  |  |  |  |  | 1.24 |
| 1000*GipSeq-burden mean | 1.01 | 1.18 | 1.15 | 1.45 | 1.35 | 1.50 | 1.38 | 1.39 | 1.30 | 1.24 |
| *Reference GipSeq-burden mean* | *0.72* | *1.06* | *0.91* | *0.95* | *1.47* | *1.78* | *1.39* | *1.65* | *1.02* | *1.12* |
| *Reference GipSeq-burden SD* | *0.02* | *0.07* | *0.07* | *0.03* | *0.07* | *0.09* | *0.1* | *0.03* | *0.05* | *0.04* |
| GipSeq-burden-Z-profile | 9.88 | 1.12 | 2.30 | 11.34 | -1.15 | -2.12 | -0.09 | -5.94 | 3.84 | 2.06 |
| GipSeq-burden-P-profile | 1.00 | 0.00 | 0.67 | 1.00 | -0.33 | -0.67 | -0.33 | -0.67 | 1.00 | 0.00 |
| Sign-burden | + | + | + | + | - | - | - | - | + | + |
| GipSeq-burden-profile | | | | | | | | | | |

Figure 14

METHOD FOR ANALYSING CELL-FREE NUCLEIC ACIDS

FIELD OF THE INVENTION

The present invention concerns the analysis of cell-free nucleic acids to determine the contribution of cell-free nucleic acids from specific tissues. In addition, the invention provides methods for diagnosing diseases based on cell-free nucleic acid analysis. The methods of the invention are also useful to detect quality defects in samples containing cell-free nucleic acids.

BACKGROUND TO THE INVENTION

Most of the nucleic acids in the body are located within cells, but a small amount of nucleic acids can also be found circulating freely in blood, urine and other bodily fluids. These nucleic acid molecules are thought to come from dying cells that release their contents into the bodily fluids as they break down. In the circulating plasma of healthy humans, cell-free DNA (cfDNA) is believed to be primarily derived from apoptosis of blood cells.

The analysis of cell-free nucleic acids allows for the non-invasive diagnosis of a number of diseases and complications as well as for non-invasive prenatal diagnosis. For example, cell-free tumour nucleic acids can be used to diagnose cancer and to detect the genetic abnormalities that are present in the underlying tumours. Cell-free nucleic acids analysis is also useful in the context of transplant rejection and pathogen detection. Another important field wherein cell-free nucleic acids are studied is prenatal diagnosis. The analysis of cell-free foetal nucleic acids in the bodily fluids of pregnant women is used to determine amongst others the sex of the foetus, the diagnosis of foetal genetic abnormalities and the foetal haplotype. Importantly, in all these instances, the analysis is based on genetic differences between two different cell populations, such as cancer genome vs. normal genome, pathogen/transplant genome vs. host genome, and foetal vs. maternal genome. As a consequence, while cell-free nucleic acid analysis provided some ground-breaking possibilities, its potential has been restricted to a few very specific applications.

Only recently, a suggestion was made that a specific analysis of cfDNA fragment lengths might be able to pinpoint a tissue of origin that contributes to the detected cfDNA fragments (WO2016/015058A2 and Snyder et al., 2016, Cell 164, 57-68). These references require the precise detection of cfDNA fragment ends and the analysis of the distribution of the fragments ends on the genome. The method has several drawbacks, including the requirement for deep sequencing of the samples in order to accurately locate fragment end distributions, large computational requirements for the analysis of sequencing data over small distances (180-200 bp) and the necessity to prevent the generation of new fragment ends due to sample storage and treatment.

Further prior art equally attempts to determine disorders such as cancer but use cfna profile from healthy persons as a reference (WO2016094853, WO2014039556).

Consequently, there is a need for novel cell-free nucleic acid analysis methods that have a broad application field and overcome the disadvantages of the prior art.

SUMMARY OF THE INVENTION

The inventors found that there are slight variations between the amounts of cell-free nucleic acids originating from different genomic locations. The quantity profiles of cell-free nucleic acids can surprisingly be used to deduce amongst others diseases as well as technical artefacts.

Therefore, methods for diagnosing a disease are presented, the method comprising:
  providing a biological sample of a subject, the sample comprising cell-free nucleic acids of the subject;
  determining for at least a part of the cell-free nucleic acids of the subject a quantity and a genomic location in a genomic region, thereby obtaining a quantity profile of cell-free nucleic acids in said genomic region;
  obtaining a reference quantity profile of cell-free nucleic acids, wherein the reference quantity profile has been derived from a biological sample obtained from a diseased reference subject;
  comparing the quantity profile with the reference quantity profile; and
  based on said comparison, determining whether the disease associated with the reference quantity profile is present in the subject.

Surprisingly, diseases that can be diagnosed by these methods include diseases which are not deletions or multiplications of a chromosome or a part thereof. For example, these methods allow for the diagnosis of diseases without an underlying genetic defect. Alternatively it concerns diseases with an underlying genetic defect at a genomic location, but wherein the quantity profile and reference quantity profile are compared at regions that do not comprise said genomic location.

Without wishing to be bound by theory, it is assumed that the degradation of cells from a tissue result in a tissue-specific cell-free nucleic acid quantity profile. Increased (or decreased) degradation of one or more specific tissues leads to an increased (or decreased) contribution of cell-free nucleic acids of the one or more specific tissues. The quantity profiles determined in a biological sample, allows to detect such increased or decreased contributions of cell-free nucleic acids originating from the specific tissue.

Furthermore methods are provided for analysing a biological sample, the comprising:
  providing a biological sample of a subject, the sample comprising cell-free nucleic acids of the subject;
  determining for at least a part of the cell-free nucleic acids of the subject a quantity and a genomic location in a genomic region, thereby obtaining a quantity profile of cell-free nucleic acids in said genomic region;
  obtaining a reference quantity profile of cell-free nucleic acids, wherein the reference quantity profile has been derived from a sample comprising an abnormal contribution of cell-free nucleic acids originating from at least one specific tissue;
  comparing the quantity profile with the reference quantity profile; and
  based on said comparison, determine whether the sample comprises an abnormal contribution of cell-free nucleic acids originating from the at least one specific tissue.

Methods are provided that allow for the identification of quantity profiles that are associated with a disease. Preferably, quantity profiles are determined for biological samples of multiple subjects, a cluster of interest is identified (e.g. an outlier cluster comprising multiple quantity profiles) and the associated disease is determined for the cluster of interest. Methods are provided for identifying a quantity profile associated with a disease, the method comprising
  providing biological samples of multiple subjects, the samples comprising cell-free nucleic acids of the subjects;

determining for at least a part of the cell-free nucleic acids of each subject a quantity and a genomic location in a genomic region, thereby obtaining for each subject a quantity profile of cell-free nucleic acids in said genomic region;

comparing the quantity profiles of the subjects using a clustering algorithm;

identifying a cluster of interest of quantity profiles;

identifying a disease present in one or more subjects from which the quantity profiles in the cluster of interest have been derived;

identifying the cluster of interest and the quantity profiles therein as being associated with said disease.

Quantity profiles from the cluster of interest or a derivative thereof may subsequently be used as a reference quantity profile in these methods for the diagnosis of a disease associated with said cluster of interest.

It has also been found that the methods disclosed herein are suitable to detect quality defects in biological samples comprising cell-free nucleic acids. For example, it has been found that certain sample treatment steps lead to detectable cell-free nucleic acid quantity profile changes. Therefore methods are provided for determining if a biological sample has a quality defect, the method comprising:

providing a biological sample of a subject, the sample comprising cell-free nucleic acids of the subject;

determining for at least a part of the cell-free nucleic acids of the subject a quantity and a genomic location in a genomic region; thereby obtaining a quantity profile of cell-free nucleic acids in said genomic region;

obtaining a reference quantity profile of cell-free nucleic acids, wherein the reference quantity profile has been derived from a biological sample with a quality defect;

comparing the quantity profile with the reference quantity profile; and based on said comparison, determine whether the biological sample has a quality defect.

The above methods are summarised in the following statements:

1. A method for analysing a biological sample, the method comprising:

providing a biological sample of a subject, the sample comprising cell-free nucleic acids of the subject;

determining for at least a part of the cell-free nucleic acids of the subject a quantity and a genomic location in a genomic region, thereby obtaining a quantity profile of cell-free nucleic acids in said genomic region;

obtaining a reference quantity profile of cell-free nucleic acids, wherein the reference quantity profile has been derived from a sample containing an abnormal contribution of cell-free nucleic acids originating from at least one specific tissue;

comparing the quantity profile with the reference quantity profile; and based on said comparison, determine whether the sample comprises an abnormal contribution of cell-free nucleic acids originating from the at least one specific tissue.

2. The method of statement 1, wherein the abnormal contribution indicates a disease originating from the at least one specific tissue.

3. The method of any one of the previous statements, wherein the quantity profile is compared with multiple reference quantity profiles to identify one or more reference quantity profiles with the highest similarity to the quantity profile.

4. The method of statement 3, wherein the comparison comprises a clustering method.

5. A method for diagnosing a disease, the method comprising providing a biological sample of a subject, the sample comprising cell-free nucleic acids of the subject;

determining for at least a part of the cell-free nucleic acids of the subject a quantity and a genomic location in a genomic region, thereby obtaining a quantity profile of cell-free nucleic acids in said genomic region;

obtaining a reference quantity profile of cell-free nucleic acids, wherein the reference quantity profile has been derived from a biological sample obtained from a diseased reference subject;

comparing the quantity profile with the reference quantity profile; and based on said comparison, determining whether the disease associated with the reference quantity profile is present in the subject.

6. The method of statement 5, wherein the disease is not a deletion or multiplication of a chromosome or a part thereof.

7. The method of any one of the previous statements, wherein the quantity and genomic location of the cell-free nucleic acids is determined by sequencing the cell-free nucleic acids and comparing them to a reference genome.

8. The method of statement 7, comprising quantifying the amount of sequence reads in a bin of a predetermined genomic size and assigning a quantity score to the bin.

9. The method of statement 8, wherein the bin has a genomic size of 500 base pairs or more.

10. A method for identifying a quantity profile associated with a disease, the method comprising providing biological samples of multiple subjects, the samples comprising cell-free nucleic acids of the subjects;

determining for at least a part of the cell-free nucleic acids of each subject a quantity and a genomic location in a genomic region, thereby obtaining for each subject a quantity profile of cell-free nucleic acids in said genomic region;

comparing the quantity profiles of the subjects using a clustering algorithm;

identifying a cluster of interest of quantity profiles;

identifying a disease present in one or more subjects from which the quantity profiles in the cluster of interest have been derived;

identifying the cluster of interest and the quantity profiles therein as being associated with said disease.

11. The method of any one of the previous statements, wherein the biological sample is a plasma sample.

12. The method of any one of the previous statements, wherein the subject is a mammal, in particular a human.

13. A method for determining if a biological sample has a quality defect, the method comprising:

providing a biological sample of a subject, the sample comprising cell-free nucleic acids of the subject;

determining for at least a part of the cell-free nucleic acids of the subject a quantity and a genomic location in a genomic region; thereby obtaining a quantity profile of cell-free nucleic acids in said genomic region;

obtaining a reference quantity profile of cell-free nucleic acids, wherein the reference quantity profile has been derived from a biological sample with a quality defect;

comparing the quantity profile with the reference quantity profile; and based on said comparison, determine whether the biological sample has a quality defect.

14. The method of statement 13, wherein the quality defect is present due to a sample treatment step.

The present invention relates to methods for determining the health status of a test individual the method comprising the steps of a) providing from said test individual a biological sample comprising cell free nucleic acids (cfna).

The test individual can be a pregnant women enrolled for genetic counseling of the foetus (sex determination, diagnosis of chromosomal deviations such as trisomies and chromosomal deletions and duplication as small as 100 kb). Apart from genetic counseling the cfna pregnant women can be diagnosis herself for genetic disorders such as chromosomal deletions and duplications as small as 100 kb, and for other disorders which result in a disease specific distribution of cfna in a blood sample. Equally these methods are equally applicable for non-pregnant women and men. Health status can thus refer to the presence or absence of a disease in a post-partum persons as well as in a foetus.

b) determining the genome wide distribution of said cell free nucleic acids over genomic locations of predetermined regions (also called partition bins) within at least the autosomes of the genome, The frequency of sequence reads over the bins is also known as bin count. Since the present inventions is not limited to genetic counseling of cfna of a foetus, and is not biased ab initio to a specific disease on a specific genomic location, or a specific set of chromosomal aberrations known in the art, the invention is typically performed on a portioning of all autosomal chromosomes, optionally including the sex chromosomes.

c) providing a set of genome wide reference distributions from a plurality of cell free nucleic acids of reference samples of reference individuals, wherein the plurality of reference individuals comprises reference individuals with a disease, The methods of the present invention are take an unbiased approach in that the bin counts of the sample cfna are compared with a collection of reference cfna which includes as well individuals with a disease as healthy persons.

d) comparing the distribution of cell free nucleic acids from said test individual of step b) with said set of reference distributions of step c), e) identifying the reference distribution which is most similar with the test distribution, f) determining based on the similarity of the test distribution with a reference distribution that the test individual has the health status of the reference individual. The methods of the invention allow an unbiased comparison of the test sample cfna with the reference samples cfna. The prior art compares test sample cfna with reference samples cfna of healthy persons whereby a difference with these reference samples indicates a disease pattern which is unknown. The methods of the present invention allow to detect the similarity of cfna of a diseased person with the cfna of a disease reference cfna. Depending on the medical record of the reference individual this may lead to an immediate diagnosis. Alternatively, additional tests can be performed on the reference individual or a biological sample thereof to compare the health status of the test individual with the reference individual.

The comparison of step d) and the determination of the most similar reference sample can be done using the GipSeq Metric Profiles and the distances between these profiles as explained below in the specification.

The methods of the present invention are especially powerful if the collection of cfna reference individual comprises a representative set of various disorders of as well genetic disorders (hereditary or acquired) and non-genetic disorders. Whereas the prior art methods are limited to large chromosomal deletions or insertions, the methods of the present invention are able to detect genomic deletion of insertion as small as 3 Mb, 2 Mb, 1 Mb, 500 kb, 250 kb or 100 kb.

The methods are not limited to autosomal chromosomes, since the sex chromosomes can equally contribute to an aberrant distribution of cfna.

The method of the present invention allow the detection of disorders such as cancers, autoimmune diseases, as well as metabolic disorders, cardiovascular disorders and other diseases wherein the degradation of tissue results in an aberrant distribution of cfna.

Since the methods of the present invention comprise preventive diagnostics such as routine cancer screening, the test individuals may be healthy persons. Accordingly the reference cfna samples will typically include samples from healthy individuals. The sequencing data of the plurality of reference samples are typically clustered. In general two approaches are followed. The first one is a clustering based on the data of the reference samples, independent from the test sample Herein similar reference distributions of individuals with a same disease are converted in a disease specific reference distribution, and wherein step d comprises comparing the distribution of the test sample with the disease specific reference distribution.

The clustering can be based on the clinical record of the patients. More typical, the data of the reference samples are clustered into groups based on similarities/distances of the bin counts of different reference samples. Hereafter the cluster can be correlated with the health/disease status of this reference. This clustering method has the advantage that reference samples which are not properly annotated with clinical data will nevertheless by clustered in the proper cluster.

Alternatively the cluster of reference distributions is generated based on the distribution of the test sample.

Herein, reference distributions of a plurality of reference individuals is converted in a test sample specific reference distribution, wherein this test sample specific reference distribution is formed by combining a group of n reference individuals with highest similarity to the test distribution.

This method leads to an increased sensitivity of determining copy number variations, and also allows to detect insertions or deletions of the genome with a size as low 5 Mb, 4 Mb, 3 Mb, 2 Mb, 1 Mb, 500 kb, 250 kb, or even as low as 100 kb.

This method also allows to group samples from individuals with unidentified diseases.

The methods of the present invention wherein the dynamic clustering method is used can be equally used in the context of prenatal diagnosis, wherein only healthy reference persons are used and/or wherein the diagnosis is limited to the sex chromosomes and or chromosomes prone to trisomies (e.g. 16 and 21).

The invention is summarised in the following statements.

1. A method for determining the health status of a test individual the method comprising the steps of a) providing from said test individual a biological sample comprising cell free nucleic acids (cfna), b) determining within at least the autosomes, the genome wide distribution of said cfna of said test individual over genomic locations of predetermined regions, c) providing a set of genome wide reference distributions of cfna from a plurality of biological samples of reference individuals, wherein the plurality of reference individuals comprises reference individuals with a disease, d) comparing the distribution of cfna from said test individual of step b) with said set of reference distributions of cfna of step c), e) identifying the reference distribution of cfna which is most similar with the distribution of cfna of the sample of the test individual, f) determining based on the similarity of the distribution of cfna of the test individual with the identified reference distribution that the test individual has the health status of the reference individual.

2. The method according to statement 1, determining in step b) the genome wide distribution within the autosomes and the sex chromosomes of the genome.

3. The method according to any one of statements 1 to 2, wherein the test individual is male or is a non-pregnant female.

4. The method according to any one of statements 1 to 3, wherein the reference individuals comprise individuals diagnosed with cancer.

5. The method according to any one of statements 1 to 4, wherein the set of references individuals comprises individuals diagnosed with a disorder selected from the group consisting of an autoimmune disease, a cardiovascular disorder and a metabolic disorders.

6. The method according to any one of statements 1 to 5, wherein the reference individuals further comprise healthy individuals.

7. The method according to any one of statements 1 to 6, wherein reference distributions of individuals with a same disease are clustered in a disease specific reference distribution, and wherein step d comprises comparing the distribution of cfna in the test sample with the disease specific reference distribution of cfna.

8. The method according to any one of statements 1 to 7, wherein reference distributions of cfna of a plurality of reference individuals are clustered in a test specific reference distribution, wherein the test specific reference distribution is generated by combining the of distributions of cfna reference samples which have the highest similarity to the distribution of cfna of the test sample. [This method is described in the application under the concept of dynamic reference set]

9. The method according to statement 8, wherein the size of the group is about (i.e. 10% less or more) the square root of the plurality of reference samples. Depending on the purpose of the method the size of the groups can be smaller and stopped as soon as there is a jump in the LOD of critical bins.

10. The method according to any one of statements 1 to 9, wherein the set of reference individual comprises individuals with a genetic disorder characterised by a genomic deletion of insertion of between 500 kb and 3 Mb.

11. The method according to statement 10, wherein a genomic deletion of insertion of between 100 kb and 5 Mb is detected.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 1: Comparison of normalization strategies sum=1 versus median=1.

FIG. 3: Simplified example of GipSeq-count and -profile for general GipSeq-cluster.

FIG. 14: GipSeq-burden(-profiles) for a general GipSeq-cluster

DETAILED DESCRIPTION OF THE INVENTION

Figure 2:
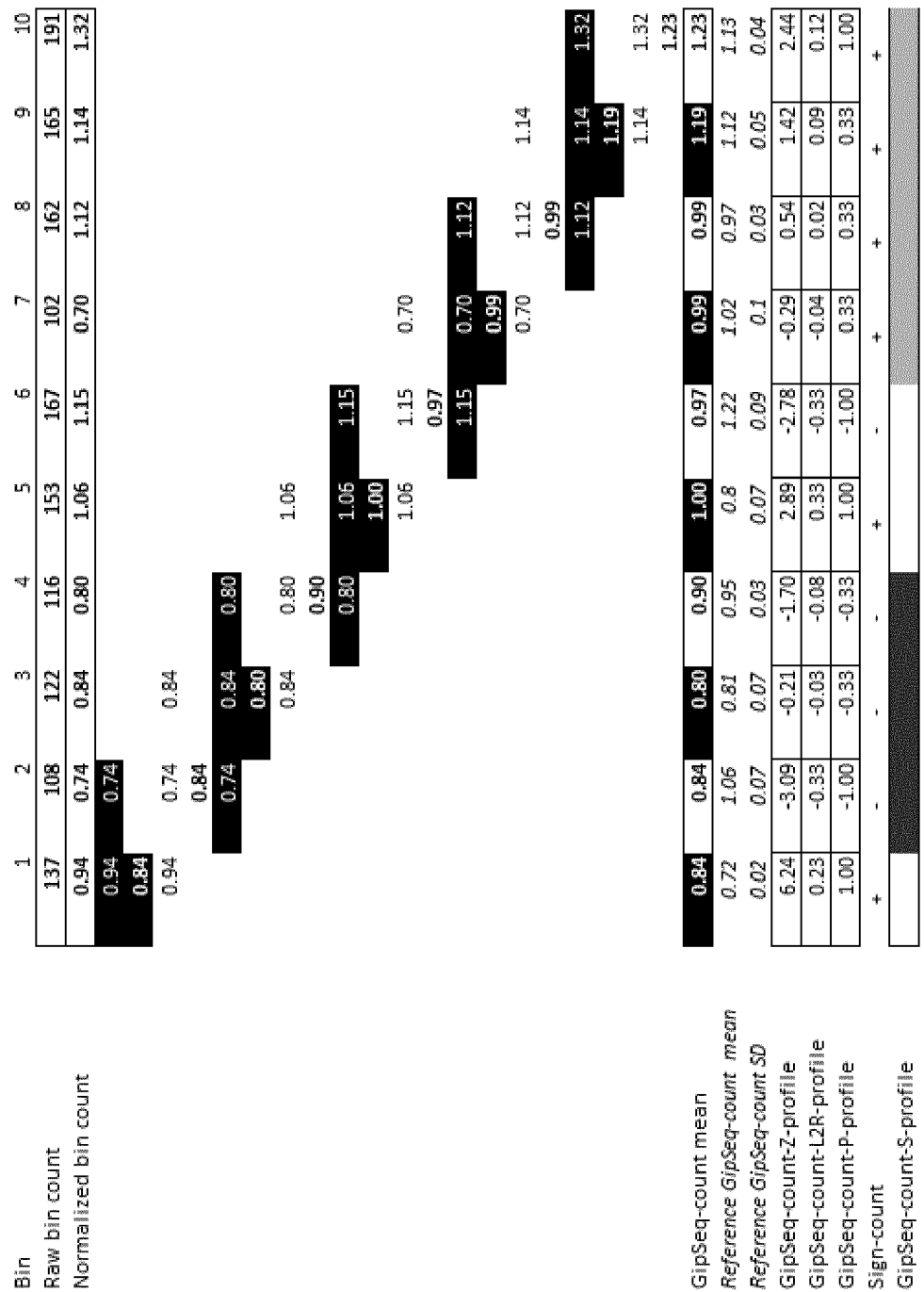
FIG. 2: GipSeq-count and -profile for singleton GipSeq-cluster.

A "biological sample" refers to any sample that is taken from a subject and that comprises cell-free nucleic acids.

The term "nucleic acid" or "polynucleotide" refers to a deoxyribonucleic acid (DNA) or ribonucleic acid (RNA) and a polymer thereof in either single- or double-stranded form. "Cell-free nucleic acids", sometimes also referred-to as circulating nucleic acids, are nucleic acids that are freely circulating in biological fluids (such as in blood or plasma).

A "subject" refers to any animal, preferably a mammal, more preferably a human. In the context of the invention, "cell-free nucleic acids of a subject" refer to the cell-free nucleic acids that originate from the subject's own genome. For example, cell-free foetal DNA molecules in a plasma sample of a pregnant female are not considered to be cell-free nucleic acids of the pregnant female, but are considered to be cell-free nucleic acids of the foetus. Similarly, cell-free nucleic acids originating from transplanted tissue in a recipient, are not considered to be cell-free nucleic acids of the recipient.

The preferred biological sample in the context of the invention is a biological fluid sample obtained from a subject, in particular a sample of urine, cerebrospinal fluid, blood or a fraction thereof. In a preferred embodiment, the biological sample is a blood sample or a fraction thereof. In a further preferred embodiment, the biological sample is a serum or plasma sample. The method of the invention may further comprise the isolation, purification and/or enrichment of cell-free nucleic acids from the biological sample. The skilled person is aware of suitable methods for performing such isolation, purification and/or enrichment and commercial kits are available to perform these.

As described herein before, the methods of the invention comprise determining for at least a part of the cell-free nucleic acids of a subject a quantity and genomic location in a genomic region, thereby obtaining a quantity profile of cell-free nucleic acids in said genomic region. The skilled person is aware of the different techniques available to determine a quantity and genomic location for cell-free nucleic acids. For example, both SNP-array genotyping and sequencing allow for the determination of the quantity and genomic location of nucleic acids. In a preferred embodiment, the genomic region under consideration in the methods of the invention is a whole chromosome or, even more preferably, a whole genome. The preferred method for determining the quantity and genomic location of cell-free nucleic acids comprises sequencing, in particular massive parallel sequencing. Sequencing is a straight-forward method that can be applied genome-wide and that allows to determine the location (based on the sequence information) as well as the amount (based on the number of reads) of cell-free nucleic acids. The methods of the invention may further comprise correcting the detected amounts of cell-free nucleic acids. For example, when using sequencing to determine the amounts, the preferred methods of the invention comprise correction of sequencing artefacts, such as by applying GC-correction. Therefore in a preferred embodiment, the methods of the invention comprise sequencing and GC correction. GC correction is known to the skilled person. A suitable method for GC correction has been described in Chen et al. (*Plos one* 2011, 6(7): e21791).

A quantity profile in the context of the invention comprises information regarding the amount of cell-free nucleic acids for several genomic locations in a genomic region. In a preferred embodiment, the quantity profile comprises information regarding the amount of cell-free nucleic acids for at least 500, in particular at least 1000, more in particular at least 2000 or at least 5000 genomic locations. In an even more preferred embodiment, the quantity profiles comprise information regarding the amount of cell-free nucleic acids for at least 10.000, in particular at least 20.000, more in particular at least 30.000 genomic locations. In another embodiment, the genomic locations are spread over at least half a chromosome, meaning that the distance between the two most distant genomic locations, for which information regarding the amount of cell-free nucleic acids is present in the quantity profile, is at least half the length of the chromosome on which they are located. In a more preferred embodiment, the genomic locations are spread over at least 75%, in particular at least 85%, more in particular at least 90% of a chromosome. In yet another embodiment, the quantity profile comprises, per chromosome, information regarding the amount of cell-free nucleic acids for at least 500 genomic locations spread over at least half of the chromosome. In particular at least 750, more in particular at least 1000, preferably at least 1500 genomic locations spread over at least half (or 75%, 85%, 90%) of the chromosome. In another embodiment, the quantity profile comprises information for at least 1 chromosome, in particular at least 2 chromosomes, preferably at least 3 chromosomes. In another preferred embodiment, the quantity profile comprises information for at least 5, in particular at least 10, at least 15, at least 20 chromosomes. Most preferably, the quantity profile comprises information for at least 22 chromosomes, in particular all autosomes. In another embodiment, the quantity profile comprises information for all autosomes and for the X chromosome. In a further embodiment, the quantity profile comprises information for all autosomes and the X and Y chromosome. "Genome-wide" in the context of the invention refers to the analysis of quantity profiles comprising information for at least all autosomes.

The information regarding the amount of cell-free nucleic acids contained in the quantity profiles may be raw amount information (e.g. raw read counts from sequencing) or processed amount information. For example, the (raw) quantity of cell-free nucleic acids that has been determined for a genomic location may be corrected and/or normalized and the derived amount information can be stored in the quantity profiles for further downstream processing. Correcting and/or normalization may improve the quality of the profiles and reduce storage and computing requirements. As described before, a preferred method for correction when using sequencing is GC correction.

It has advantageously been found that storage and computing requirements can be reduced drastically by partitioning the genomic region into genomic locations that span several bases (bins). Therefore, in a particular embodiment, determining a quantity profile of cell-free nucleic acids comprises quantifying the amount of cell-free nucleic acids in a bin of a predetermined genomic size and assigning a quantity score to the bin. Preferably, the bin has a width of a predetermined amount. Based on the disclosure of the present invention and his general knowledge, the skilled person can determine a suitable bin width, e.g. based on the computing power and data storage that is available. In a particular embodiment, the bin width is at least 500, in particular at least 1000, more in particular at least 2000 bases. Preferably, the bin width is at least 5000, in particular at least 10.000, more in particular at least 20.000 bases. In such case, one bin represents a genomic location within a genomic region covering several bins. For example, taking a bin width of 50.000 bases, a genome-wide analysis of all 22 autosomes would result in about 61.927 bins. The obtained quantity profile contains information for the quantity/amount of cell-free nucleic acids in the various bins (genomic locations). When performing sequencing to determine the amount and genetic location of the cell-free nucleic acids, the methods of the present invention preferably comprise quantifying the amount of sequence reads in a bin of a predetermined size and assigning a quantity score to the bin.

In another embodiment, cell-free nucleic acid quantity values are normalized. When applying a correction step, such as GC correction, normalization is preferably performed after the correction step. Different quantity normalization techniques are known to the skilled person. For example, normalization may be executed such that the sum of normalized quantity values is a predetermined value (e.g. 1). Alternatively, and preferably in the present invention, the determined amount of cell-free nucleic acids is normalized such that the median of normalized values is a predetermined value.

In the methods of the invention, a quantity profile determined for a sample of interest will generally be compared to a reference quantity profile. The reference quantity profile is derived from a (reference) sample. As is known to the skilled person, a (reference) sample is a sample with a known feature, such as the presence or absence of an aberration. For example, in the context of diagnosing a disease, the reference sample may be a biological sample obtained from a subject with the disease. In some embodiments, the sample is derived from a primary tissue from a diseased subject. In other embodiments, the sample is derived from a primary tissue from a healthy subject. In some embodiments, the sample for establishing a reference quantity profile is derived from an immortalized cell line. In the context of determining whether a sample comprises an abnormal contribution of cell-free nucleic acids from a specific tissue, the reference sample may be a sample containing an abnormal contribution of cell-free nucleic acids originating from the specific tissue. Such a reference sample may be constructed in vitro, e.g. by generating in vitro cell-free nucleic acids from a specific tissue to obtain a sample with an increased contribution of cell-free nucleic from said specific tissue. Alternatively, the reference sample is a biological sample obtained from a subject for which it is known that the sample will contain an abnormal contribution of cell-free nucleic acids. For example, the subject may suffer from a disease with increased tissue damage or apoptosis, resulting in abnormal contributions of cell-free nucleic acids originating from said tissue. In the context of determining a quality defect, the reference quantity profile may be derived from a (biological) sample with a known quality defect. In a particular further embodiment, the reference quantity profile may be derived from a sample that underwent a specific sample treatment step. For example, the reference sample may be a sample that was kept for a specific time at non-optimal temperature conditions. In addition, reference quantity profiles may be derived from a 'standard' (biological) sample, e.g. a sample obtained from a healthy individual, a sample without an abnormal contribution of cell-free nucleic acids from a specific tissue, or a sample without a quality defect.

As will be understood by the skilled person, a reference may be derived from one or more reference samples. Therefore, in the context of the invention, a reference quantity profile being derived from a (biological) sample means that the reference quantity profile is derived from at least one (biological) sample. For example, quantity profiles may be determined for multiple samples and these quantity profiles may be further processed (e.g. by averaging them or by determining allowable deviations between the quantity profiles) to obtain a reference quantity profile. Alternatively, quantity profiles may be determined for multiple samples and retained as a set of reference quantity profiles. A comparison between the quantity profile and the set of reference quantity profiles may be performed in subsequent steps of the methods of the invention. The use of multiple reference quantity profiles is especially useful when the comparison step comprises a clustering method. In a preferred embodiment, multiple reference samples are used, in particular at least 50 reference samples, more in particular at least 100, even more in particular at least 200. In a further embodiment, the reference quantity profile is derived from at least 100, in particular at least 200, more in particular at least 500 (biological) samples. Of particular interest is the use of the present invention in the context of large data sets of cell-free nucleic acid samples, e.g. hundreds or thousands of samples. For example, the present invention may be applied on at least hundred, preferably at least thousand, plasma or serum samples. The present invention provides a straightforward method that allows to retrieve biologically relevant information from thousands of samples with the use of relatively limited computing power.

In a particular embodiment, multiple reference quantity profiles are used, wherein a part of the reference quantity profiles is derived from a sample with a known aberration and a part of the reference quantity profiles is derived from a standard sample without an aberration. Comparison of the quantity profiles with such multiple reference quantity profiles allows one to determine if the quantity profile is more similar to the reference quantity profiles associated with the reference sample with the aberration or with standard reference sample without the aberration. In these embodiments, the method further comprises determining if the sample comprises the aberration based on said comparison.

A variety of statistical methods can be applied to compare the quantity profiles described herein. The skilled person is aware of suitable comparison methods. In a preferred embodiment, comparing quantity profiles comprises a clustering method. Clustering is a statistical technique for identifying similarity groups in data invoked clusters. For example, clustering groups (i) data instances similar to (near) each other in one cluster, and (ii) data instances different from (far away) each other into different clusters. Clustering often is referred to as an unsupervised learning task as no class values denoting an a priori grouping of the data instances normally are provided, where class values often are provided in supervised learning.

In certain embodiments, data clustering algorithms can be hierarchical. Hierarchical algorithms often find successive clusters using previously established clusters. These algorithms can be agglomerative ("bottom-up") or divisive ("top-down"), for example. Agglomerative algorithms often begin with each element as a separate cluster and often merge them into successively larger clusters. Divisive algorithms often begin with the whole set and often proceed to divide it into successively smaller clusters. Partitional algorithms typically determine all clusters at once or in iterations, but also can be used as divisive algorithms in the hierarchical clustering. Density-based clustering algorithms can be devised to discover arbitrary-shaped clusters. In this approach, a cluster often is regarded as a region in which the density of data objects exceeds a threshold. DBSCAN and OPTICS are two typical algorithms of this kind, for example. Two-way clustering, co-clustering or biclustering are clustering methods where not only the objects are clustered but also the features of the objects, i.e., if the data is represented in a data matrix, the rows and columns are clustered simultaneously, for example. Spectral clustering techniques often make use of the spectrum of the data similarity matrix to perform dimensionality reduction for clustering in fewer dimensions. Some clustering algorithms require specification of the number of clusters in the input data set, prior to execution of the algorithm. Barring knowledge of the proper value beforehand, the appropriate value must be determined, a problem for which a number of techniques have been developed.

In other clustering embodiments, one step is to select a distance measure, which will determine how the similarity of two elements is calculated. This selection generally will influence the shape of the clusters, as some elements may be close to one another according to one distance and farther away according to another. For example, in a 2-dimensional space, the distance between the point (x=1, y=0) and the origin (x=0, y=0) is 1 according to usual norms, but the distance between the point (x=1, y=1) and the origin can be 2, square root of 2 or 1 based on the 1-norm, 2-norm or infinity-norm distance, respectively.

In certain embodiments, several types of algorithms can be used in partitional clustering, including, but not limited to, k-means clustering, fuzzy c-means clustering, and QT clustering. A k-means algorithm often assigns each point to a cluster for which the centre (also referred to as a centroid) is nearest. The centre often is the average of all the points in the cluster, that is, its coordinates often are the arithmetic mean for each dimension separately over all the points in the cluster. Examples of clustering algorithms include, but are not limited to, AGNES, CLARANS, PAM, CLATIN, CLARA, DBSCAN, BIRCH, WaveCluster, CURE, CLIQUE, OPTICS, K-means algorithm, and hierarchical algorithm.

Therefore, in a particular embodiment, the (sample) quantity profile is compared with multiple reference quantity profiles to identify one or more reference quantity profiles with the highest similarity to the quantity profile. The methods of the invention may further comprise determining that the sample comprises a known feature of the one or more reference quantity profiles with the highest similarity. Thus, in a particular embodiment, the methods of the invention comprise clustering a quantity profile and multiple reference quantity profiles with a known feature (e.g. corresponding to a known disease, an abnormal contribution of a specific tissue or a known quality defect) and, if said quantity profile cluster together with one or more of the reference quantity profiles, determine that the known feature is present in the sample from which the quantity profile has been determined.

As described herein above, the methods of the present invention are suitable to determine if a sample comprises an abnormal contribution of cell-free nucleic acids originating from a specific tissue. In a particular embodiment, the method further comprises providing an instruction to perform a diagnostic test for a disease associated with the specific tissue. For example, if an increased contribution of cell-free nucleic acids originating from liver tissue is determined in the sample, the methods of the invention may further comprise instructing a diagnostic test to determine the disease causing the abnormal contribution, such as liver cirrhosis, hepatitis or liver cancer. In another embodiment, the abnormal contribution indicates a disease originating from the at least one specific tissue. The methods of the invention may comprise the further step of diagnosing the subject as having a specific tissue disease.

As described herein above, the methods of the invention may comprise comparing a quantity profile with a reference quantity profile that has been derived from a biological sample obtained from a diseased reference subject and, based on the comparison, determine whether the disease associated with the reference quantity profile is present in the subject. As will be understood by the present disclosure, the methods of the invention unexpectedly allow using cell-free nucleic acids for diagnosing diseases that are not associated with deletions or multiplications of a chromosome or a part thereof, such as aneuploidy. In addition, the methods of the present invention can be applied without relying on genetic differences between multiple genomic contributions within a sample, such as the difference between foetus and pregnant woman or between organ donor and recipient.

Therefore, in a particular embodiment, the quantity profile is obtained by determining for at least a part of the cell-free nucleic acids a quantity and a genomic location in a genomic region, without relying on genetic variations between cell-free nucleic acids that have the same genomic location. In another embodiment, the methods of the present invention do not rely on a genetic variation between cell-free nucleic acids originating from different genomic contributions. In a further embodiment, the methods of the present invention do not rely on a genetic variation between healthy and non-healthy tissue (e.g. aneuploidic cells), foetal and maternal genomes, or organ donor and recipient genomes.

In another particular embodiment, the disease as used throughout this document is not a deletion or multiplication of a chromosome or part thereof. In a further particular embodiment, the disease is not a genetic disease, such as aneuploidy. In an alternative embodiment, the subject is not suspected of having a disease with an underlying genetic aberration.

In a particular embodiment, the subject is diagnosed presymptomatically, i.e. before the subject observed symptoms from the disease. In addition, the methods of the present invention may be applied on a sample from a subject for which cell-free nucleic acids are analysed for a different purpose. For example, the methods of the present invention may be applied on a sample of a pregnant female undergoing a prenatal diagnostic test. While the primary reason for the test may be to diagnose the foetus, the methods of the invention may identify a (e.g. presymptomatic) disease in the pregnant female. Therefore, in a particular embodiment, the subject is a pregnant female. In a further particular embodiment, the sample is obtained from a pregnant female and the disease is not a disease present in the embryo or foetus. In another particular embodiment, the subject is a pregnant female and the disease is not associated with the pregnancy.

If it has been determined that a disease is associated with the quantity profile of the subject, said quantity profile may be used as a reference quantity profile for diagnosing the disease in another subject. Thus, the present invention allows to iteratively improve a set of reference quantity profiles or the reference quantity profile derived from such a set.

Identifying a Quantity Profile Associated with a Disease

As described herein above, the present invention may comprise providing biological samples of multiple subjects, the samples comprising cell-free nucleic acids of the subjects;

determining for at least a part of the cell-free nucleic acids of each subject a quantity and a genomic location in a genomic region, thereby obtaining for each subject a quantity profile of cell-free nucleic acids in said genomic region;

comparing the quantity profiles of the subjects using a clustering algorithm;
identifying a cluster of interest of quantity profiles;
identifying a disease present in one or more subjects from which the quantity profiles in the cluster of interest have been derived;
identifying the cluster of interest and the quantity profiles therein as being associated with said disease.

In a further embodiment, biological samples of at least 20, in particular at least 50, at least 100, at least 200 subjects are provided. In a preferred embodiment, quantity profiles for at least 500 samples are determined and compared using the clustering algorithm. In this method of the invention, a disease may be determined retroactively in subjects from which the quantity profiles in the cluster of interest have been derived.

In another further embodiment, the cluster of interest and/or the quantity profiles therein that has been identified as being associated with a disease is used as a reference quantity profile or a cluster of reference quantity profiles for said disease. The reference quantity profile derived from the cluster of interest or the quantity profiles therein may be used in the methods of the invention as described herein.

Determining a Quality Defect

As described herein above, the methods of the invention may be used to determine a quality defect by
providing a biological sample of a subject, the sample comprising cell-free nucleic acids of the subject;
determining for at least a part of the cell-free nucleic acids of the subject a quantity and a genomic location in a genomic region; thereby obtaining a quantity profile of cell-free nucleic acids in said genomic region;
obtaining a reference quantity profile of cell-free nucleic acids, wherein the reference quantity profile has been derived from a biological sample with a quality defect;
comparing the quantity profile with the reference quantity profile; and
based on said comparison, determine whether the biological sample has a quality defect.

In a particular embodiment, the quality defect is present due to a sample treatment step. For example, storing the sample at a non-optimal temperature may cause signature changes in the quantity profiles of cell-free nucleic acids. The methods of the invention allow determining such quality defects. The methods of the invention may further comprise instructing to discard the sample for subsequent analysis and optionally to obtain a new sample from the subject.

In another particular embodiment, the methods of the invention are implemented on a computer. In a particular embodiment, the present invention provides a computer program product comprising computer program code means adapted for performing the steps of the method as described above, when the computer program product is run on a computer. In a preferred embodiment, the computer program code is adapted for determining a quantity profile based on information of cell-free nucleic acids from a sample of a subject. In a further embodiment, the computer program code is also adapted for comparing the determined quantity profile with a reference quantity profile. The computer program may further determine whether a biological sample has a feature present in the reference quantity profile based on the comparison.

In another embodiment, the present invention provides a data carrier storing a computer program product according to the invention. The term "data carrier" is equal to the terms "carrier medium" or "computer readable medium", and refers to any medium that participates in providing instructions to a processor for execution. Such a medium may take many forms, including but not limited to, non-volatile media, volatile media, and transmission media. Non-volatile media include, for example, optical or magnetic disks, such as a storage device which is part of mass storage. Volatile media include dynamic memory such as RAM. Common forms of computer readable media include, for example, a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the internet. Transmission media can take the form of acoustic or light waves, such as those generated during radio wave and infrared data communications. Transmission media include coaxial cables, copper wire and fibre optics, including the wires that form a bus within a computer.

In another embodiment, the present invention provides in transmission of a computer program product according to the invention over a network. As will be understood by the skilled person, part of the steps of the methods of the invention may be carried out on a remote server. As a mere example, (a) computing of a quantity profile based on determined quantities and genomic locations of cell-free nucleic and/or (b) comparing a quantity profile with a reference quantity profile may be executed on a local computer or on a remote server.

Genome Partitioning

A set of genomic locations of a predetermined genomic size (herein referred to as a bin) is defined that form a partitioning of the chromosomes of the genome. All bins except the potentially smaller ones at the end of each chromosome span a region of a fixed width. In this example, we used a fixed bin width of 50000 bases, which results in 61 927 bins.

The bin count of a sequenced sample S, given a partitioning of the genome P, contained for each bin B in partitioning P a GC-corrected and normalised count of sequencing reads originating from sample S and starting in bin B. GC-correction was performed per sample according to [Chen et al., PLOS paper, 2011].

To normalize the GC-corrected bin counts per sample they were divided by the median of all GC-corrected bin counts of the sample. As such, this normalisation aims at median=1 and is more robust than the most common strategy, which aims at sum=1 via division by the sum of all GC-corrected bin counts.

FIG. 1 is a schematic overview to help clarify the key difference between these two approaches. In this schematic overview there are 10 bins. The left table shows the statistics for sample A: GC-corrected bin counts and the result of both normalization strategies. The middle table shows stats for a second sample B. Notice the GC-corrected counts for B are identical to those in A except for the first bin, which has increased by the sum of A bin counts. As a consequence, the sum of bin counts in B has doubled compared to A. The right table in FIG. 1 shows the impact of this isolated increase on the other bins. Notice the sum=1 normalization results in a 50% decrease of the other bins whereas with the median=1 normalization this decrease is limited to 6%. So, a true substantial gain in a single bin would trigger genome wide artificial substantial losses with the sum=1 approach. With the median=1 approach however this compensation effect is largely suppressed.

Samples

A GipSeq-cluster is defined in this example as a non-empty set of sequenced samples.

Samples can be grouped into GipSeq-clusters for various purposes. The main distinction is between sets that are:

1. manually constructed: e.g., to organise samples per customer or sequencing run, to create reference sets, or to combine samples sharing a particular phenotype 2. automatically constructed: e.g., as a result of applying an unsupervised clustering algorithm The operations and examples below are stated in terms of GipSeq-clusters. Notice they also apply to single samples, as these can be cast as a special case of GipSeq-clusters that contain exactly one sample.

Determining a Quantity Profile

The GipSeq-count of a GipSeq-cluster C, given a partitioning of the genome P, contained for each bin B in partitioning P the mean and standard deviation (SD) of bin counts observed across the samples of C in a fixed sized window of bins with bin B at the centre.

Virtual bins were added to the start and end of each chromosome to make the above definition work for the leading and trailing bins. These virtual bins were ignored in calculations of the mean and SD scores.

For computing GipSeq-counts we used a fixed window of 21 bins. Combined with the 50 kb bin size this means we included a context of 10*50 kb=500 kb to the left and the right of each bin. For leading (resp. trailing) bins the left (resp. right) context reduces to zero. As a consequence, GipSeq-counts were based on a region between 550 kb and 1050 kb.

The GipSeq-count concept is illustrated in FIG. 2. For convenience, the GipSeq-cluster in the figure is a singleton, the number of bins on the chromosome is set to ten and the fixed window size to three bins. The first three rows show the bin index, the GC-corrected number of reads per bin, and the normalized bin count as described above. The GipSeq-count for the first bin (in bold on row 4) is based on an incomplete window spanning the first two bins (and a virtual bin 0):

$$\text{gipseq\_count}_1 = \text{mean}\{0.94, 0.74\} = 0.84$$

From bin 2 to 6, GipSeq-counts are based on complete (=size 3) windows, e.g., for bin 2:

$$\text{gipseq\_count}_2 = \text{mean}\{0.94, 0.74, 0.84\} = 0.84$$

GipSeq-counts for bin 10 are again based on an incomplete window, spanning the final 2 bins (and a virtual bin 11).

FIG. 3 shows how GipSeq-counts can be calculated for GipSeq-clusters of any size, in this case 2. In this generic setting, each GipSeq-count is calculated as the mean of nr_samples*window_size bin counts. For instance, the GipSeq-count for bin 2 is now based on 2*3 bin counts:

$$\text{gipseq\_count}_2 = \text{mean}\{0.66, 1.19, 0.67, 0.94, 0.74, 0.81\} = 0.84$$

The possibility to calculate GipSeq-counts for GipSeq-clusters of any size is important for the construction and application of reference sets, which in turn enable the calculation of a GipSeq-profile.

Let P be a partitioning of the genome and let RC be a GipSeq-cluster that is used as a reference set. Then the GipSeq-Z-profile of a GipSeq-cluster C w.r.t. reference set RC contains for each bin B in partitioning P the deviation of the GipSeq-count G for that bin in C relative to the GipSeq-count RG for that same bin in RC. The deviation is calculated as the $$Z\text{-score} = (\text{mean}(G) - \text{mean}(RG))/sd(RG)$$

Both FIG. 2 and FIG. 3 show the calculation of the GipSeq-Z-profile near the bottom. For instance, for bin 1 the GipSeq-count reference set has mean 0.72 and SD 0.02. In FIG. 2, the GipSeq-count mean observed in the GipSeq-cluster is 0.88 and the Z-score is 6.24.

The sign of the Z-score can be used to detect gains (positive Z) and losses (negative Z) w.r.t. a reference set. The idea underlying a GipSeq-profile is that real gains and losses of substantial length should show up as sufficiently long sequences of bins where the sign of the Z-score is constant.

Normalization of Quantity Profiles

The GipSeq-profile of a GipSeq-cluster w.r.t. a reference set is a function of the GipSeq-Z-profile where the Z-score in each bin is replaced by one of the three following values:

Gain: the bin is part of a sequence of minimally L bins with a positive Z-score

Loss: the bin is part of a sequence of minimally L bins with a negative Z-score

Neutral: otherwise

We used L=40 as the minimal length (in number of bins) of gains and losses. In combination with a 50 kb bin size this means we target gains and losses of minimally 2 Mb. The bottom row in FIG. 2 and FIG. 3 show the GipSeq-profile with L=3 as a minimum length for gains and losses. Notice for instance in FIG. 2, that bins 1, 5, and 6 are neutral, bins 2 to 4 constitute a loss and bins 7 to 10 a gain. To the extent the GipSeq-profiles of two GipSeq-clusters correspond to real gains and losses observed in those clusters, we can express the similarity between their genome wide imbalance profiles as a similarity between their GipSeq-profiles.

Comparing Quantity Profiles with Reference Quantity Profiles

The similarity between two GipSeq-profiles determined using the fraction of counted bins that match. Counted bins are those that remain after removal of the bins that are neutral in both GipSeq-profiles. Matching bins are those that have identical values in both GipSeq-profiles, i.e. that are either both gain or both loss.

Notice that each GipSeq-profile is 100% similar to itself, and that the similarity metric is symmetrical.

Figure 4:
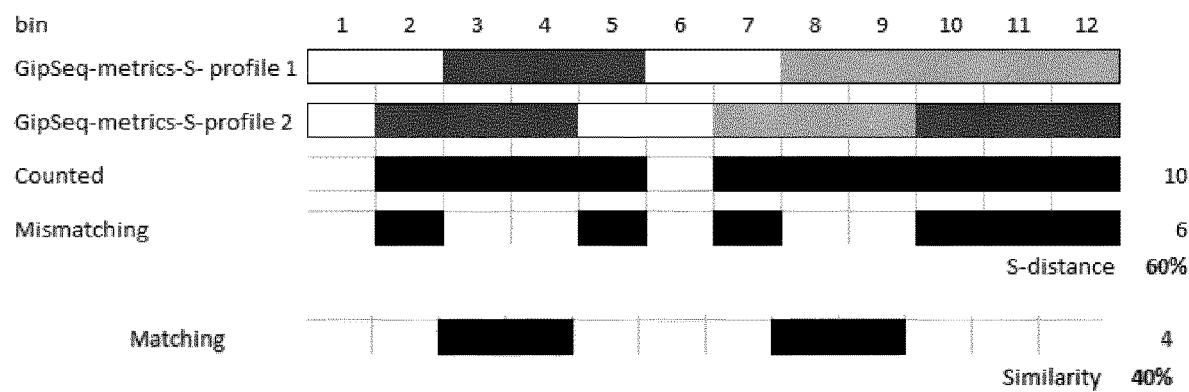
FIG. 4: Simplified example of similarity between two GipSeq-profiles.

As an example, consider the two 12-bin GipSeq-profiles in FIG. 4, again with minimum length of gains and losses L=3. The first and sixth bins were ignored as they were neutral in both GipSeq-profiles. This leaves 10 bins that are counted. Of those 10 bins, only bins 3, 4, 8, and 9 have identical values. So 4 out of 10 bins are matching, which translates to a similarity of 40%.

A partitioning of a genome is a set of regions that form a partitioning of the chromosomes of the genome. Each region in this set is called a partition bin. All partition bins except the potentially smaller ones at the end of each chromosome span a region of a predefined width.

By default, we use a fixed bin width of 10000 bases, which—with genome build hg38 restricted to the 24 chromosomes—results in 308839 partition bins.

A ROI-list of a genome is a set of genomic intervals considered to be Regions Of Interest (ROI). These so-called ROI bins can vary in size and correspond to a whole chromosome, a chromosome arm, a disease associated genomic region, or any other interval deemed worth reporting.

Our default ROI list contains 24 chromosomes, 48 chromosome arms, 48 telomeric regions (2 Mb) at both sides of the chromosomes, and 57 disease associated regions. ROI bins are allowed to overlap and contain other bins. In particular the larger ROI bins contain a subset of the partition bins.

The raw bin count of a sequenced sample S contains for each bin B from the union of partition bins and ROI bins a count of sequencing reads originating from sample S and starting in bin B. [Optionally, GC-correction is performed per sample according to [Chen et al., PLOS paper, 2011]. The default is not to use any GC-correction of the raw bin counts]

The normalized bin count of a sequenced sample contains for each bin B from the union of partition bins and ROI bins a normalized count obtained by dividing the raw bin count of bin B by the median of all partition bin counts of the sample.

This normalization aims at median=1 for the partition bins, and is more robust than the most common strategy, which aims at sum=1 via division by the sum of all partition bin counts.

The artificial example in FIG. 1 may help to clarify the key difference be-tween these two approaches. In the example there are 10 bins. The left table shows the statistics for sample A: bin counts and the result of both normalization strategies. The middle table shows stats for a second sample B. Notice the bin counts in the first column for B are identical to those in A except for the first bin, which has increased by the sum of A bin counts. As a consequence, the sum of bin counts in B has doubled compared to A. The right table in FIG. 1 shows the impact of this isolated increase on the other bins. Notice the sum=1 normalization results in a 50% decrease of the other bins whereas with the median=1 normalization this decrease is limited to 6%. So, a true substantial gain in a single bin would trigger genome wide artificial substantial losses with the sum=1 approach. With the median=1 approach however this compensation effect is largely suppressed.

The bin mutation burden of a sequenced sample S contains for each bin B from the union of partition bins and ROI bins the mean normalized number of genomic alterations observed in sequencing reads originating from sample S and starting in bin B. To normalize, the number of genomic alterations is divided by the read length. In the output of sequence aligner BWA the number of genomic alterations {also known as edit distance{for each read can be found in the NM field.

A GipSeq-cluster is a non-empty set of sequenced samples.

Samples can be grouped into GipSeq-clusters for various purposes. The main distinction is between sets that are:
1. manually constructed: e.g., to organize samples per customer or sequencing run, to create fixed reference sets, or to combine samples sharing a particular phenotype
2. automatically constructed: e.g., via unsupervised clustering, or by selecting a dynamic reference set of samples that look similar to a sample of interest The operations and definitions below are stated in terms of GipSeq-clusters. Notice they also apply to single samples, as these can be cast as a special case of GipSeq-clusters that contain exactly one sample.

The GipSeq-metrics of a GipSeq-cluster C contain for each bin B from the union of partition bins and ROI bins the mean and standard deviation (SD) of
the normalized bin counts (GipSeq-count of C), and
mean mutation burden (GipSeq-burden of C)

observed across the samples of C. For partition bins these metrics are calculated in a fixed sized window that has bin B at the centre.

Virtual partition bins are added to the start and end of each chromosome to x the above definition for the leading and trailing partition bins. These virtual, empty partition bins are ignored in calculations of the mean and SD scores.

For computing GipSeq-metrics of partition bins we use a default fixed window of 101 partition bins. Combined with the default 10 kb bin size this means we include a context of 50×10 kb=500 kb to the left and the right of each partition bin. For leading (resp. trailing) partition bins the left (resp. right) context reduces to zero. As a consequence, GipSeq-metrics of partition bins are typically based on a 1010 kb region. Towards chromosome borders this size gradually decreases to reach a minimum of 510 kb.

Figure 12:
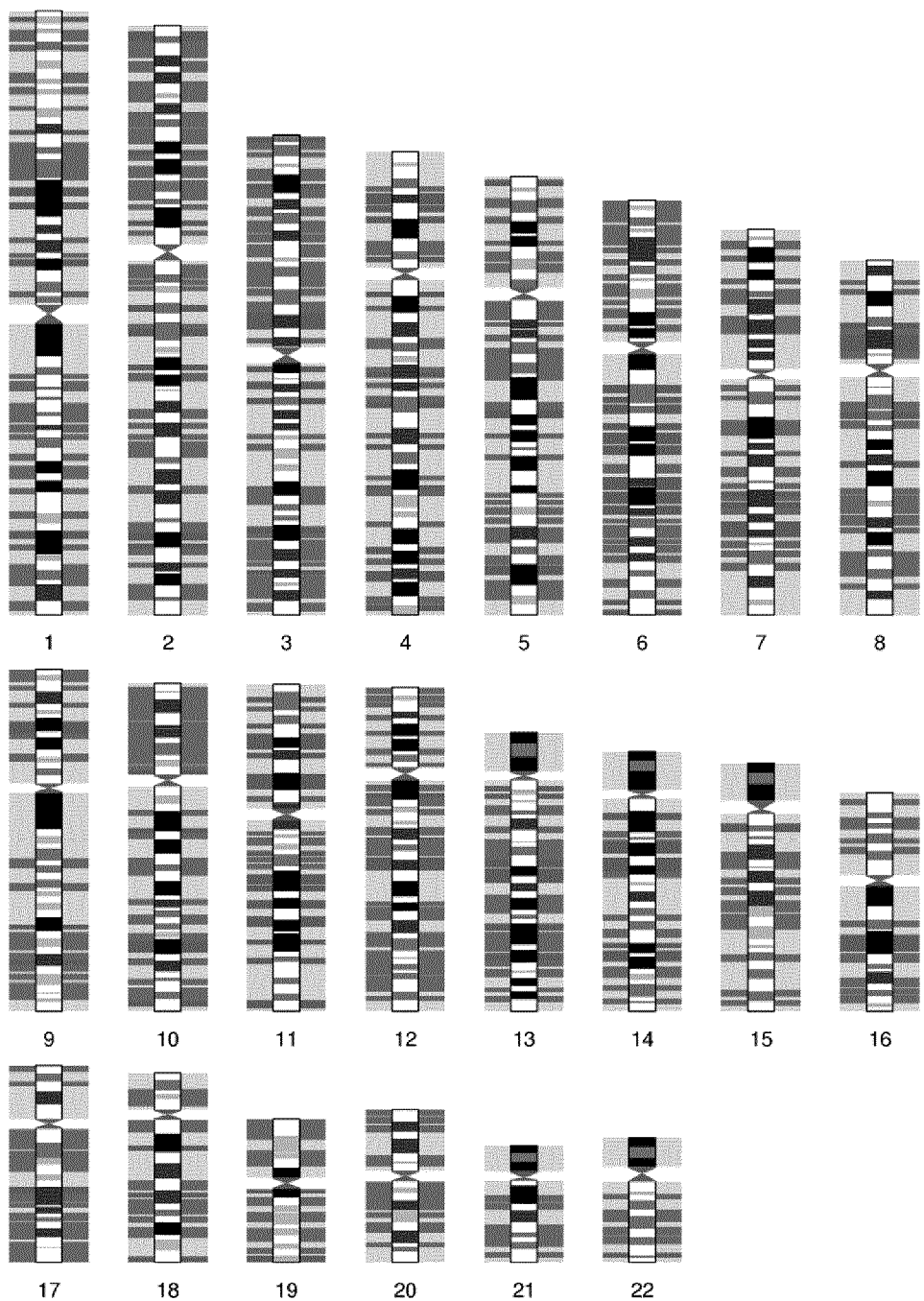
FIG. 12: GipSeq-profile of Hamilton-processed samples.
Figure 13:
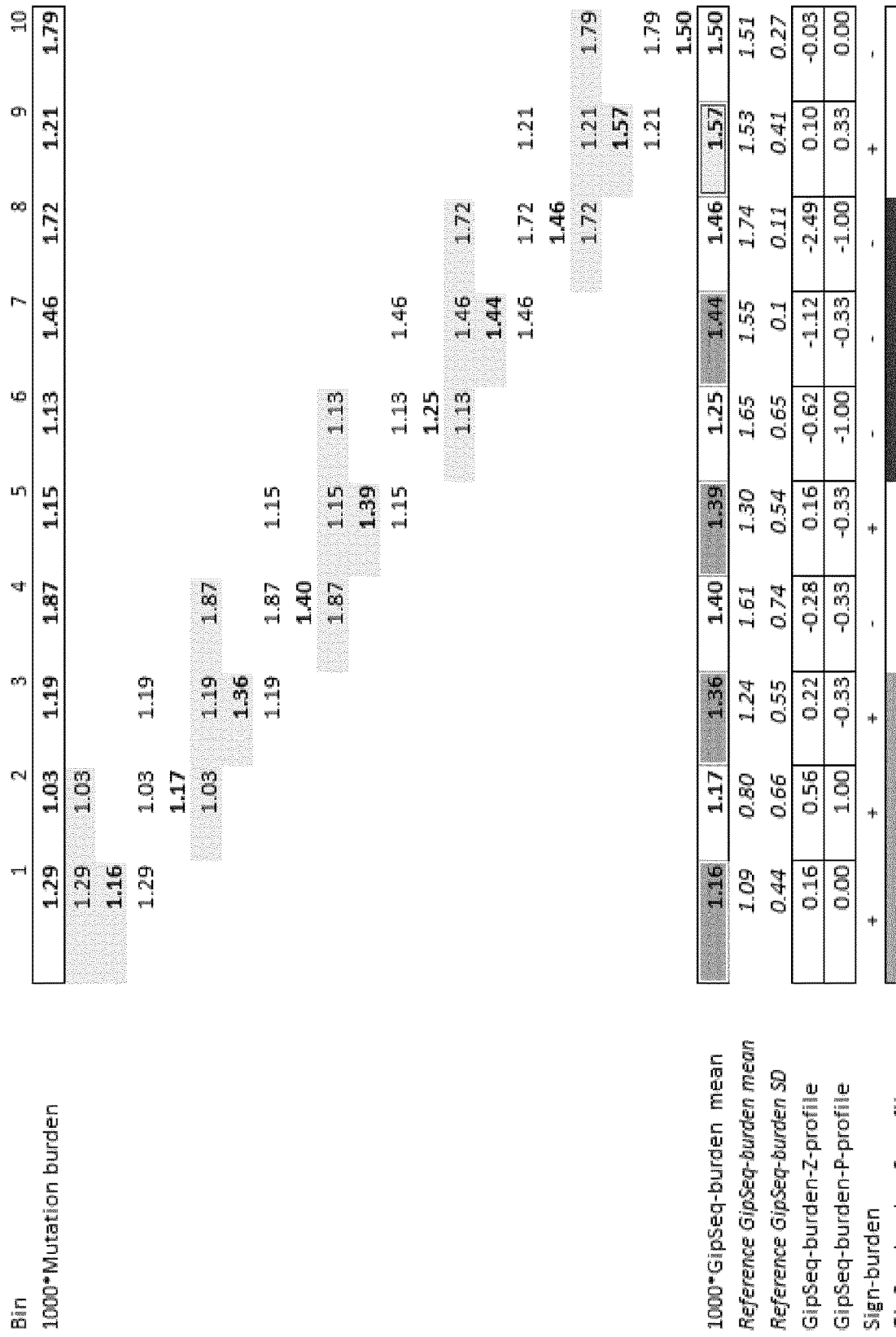
FIG. 13: GipSeq-burden(-profiles) for a singleton GipSeq-cluster

The GipSeq-metrics concept as it applies to partition bins is illustrated in FIG. 12 (GipSeq-count) and 13 (GipSeq-burden).

For convenience, the GipSeq-cluster is a singleton, the number of partition bins on the chromosome is set to ten and the fixed window size to three bins.

In FIG. 2, the first three rows show the bin index, the raw bin count, and the normalized bin count as defined above. The GipSeq-count for the first bin (in bold on row 5) is based on an incomplete window spanning the first two bins (and a virtual bin 0):

$$\text{gipseq count}_1 = \text{mean}\{0.94, 0.74\ g\} = 0.84$$

From partition bin 2 to 6, GipSeq-counts are based on complete (=size 3) windows, e.g., for bin 2:

$$\text{gipseq count}_2 = \text{mean}\{0.94, 0.74, 0.84\} = 0.84$$

GipSeq-counts for partition bin 10 are again based on an incomplete window, spanning the final 2 bins (and a virtual bin 11).

FIGS. 3 and 14 show how GipSeq-metrics can be calculated for GipSeq-clusters of any size, in this case two samples. In this generic setting, each GipSeq-metric is derived from nr_samples*window_size bin metrics. For instance, the GipSeq-count for bin 2 is now based on 2*3 bin counts:

$$\text{Gipseq\_count}_2 = \text{mean}\{0.66, 1.19, 0.67, 0.94, 0.74, 0.81\} = 0.84$$

The possibility to calculate GipSeq-counts for GipSeq-clusters of any size is crucial for the construction and application of reference sets, which in turn enable the calculation of a GipSeq-profile.

The GipSeq-metrics-Z-profile—where metrics can be count or burden- of a GipSeq-cluster C w.r.t. reference set RC contains for each bin 8 from the union of partition bins and ROI bins the deviation of the GipSeq-metrics mean for that bin in C relative to the GipSeq-metrics for that same bin in RC. The deviation is calculated as the Z-score of the metrics, where $$Z = \frac{\text{mean}(C) - \text{mean}(RC)}{SD(RC)}$$

FIGS. 2, 3, 13, 14 show the calculation of the GipSeq-metrics-Z-profile for partition bins near the bottom. For instance, in FIG. 2 for partition bin 1 the GipSeq-count reference set has mean 0.72 and SD 0.02, the GipSeq-count mean observed in the GipSeq-cluster is 0.88 and the Z-score is 6:24.

The GipSeq-count-L2R-profile of a GipSeq-cluster C w.r.t. reference set RC contains for each bin B from the union of partition bins and ROI bins the log 2 ratio of the GipSeq-count mean for that bin in C and the GipSeq-count mean for that same bin in RC.

FIGS. 2 and 3 show the GipSeq-count-L2R-profiles of a cluster with one and two samples respectively.

The GipSeq-metrics-P-profile—where metrics can be count or burden- of a GipSeq-cluster C w.r.t. reference set RC contains for each partition bin B the scaled percentage of bin values that are lower than the GipSeq-metrics mean for that same bin in RC. Scaling to interval [−1,1] is done with formula scale(x)=1−2*x such that bins where all values are above (below) the cluster mean get score 1 (−1). Score 0 would indicate half of the bin values are above and half are below the cluster mean.

Essentially, the GipSeq-metrics-P-profile contains for each partition bin the percentile rank of the cluster mean in the set of all values observed in the bin window.

The sign of the GipSeq-count-Z-score of partition bins indicates gains (positive Z) and losses (negative Z) w.r.t. a reference set. Likewise, the sign of GipSeq-burden-Z-scores can be interpreted as regional mutation burden rises (positive Z) and falls (negative Z). The idea underlying the GipSeq-metric-S-profile defined below is that real deviations of substantial length should show up as sufficiently long sequences of bins where the sign of the Z-score is constant.

The GipSeq-metrics-S-profile of a GipSeq-cluster w.r.t. a reference set is a function of the GipSeq-metric-Z-profile where the Z-score in each partition bin is replaced by one of the three following values bases on the sign (S) of the Z-score:
  Increase: the partition bin is part of a sequence of minimally L bins with a positive Z-score
  Decrease: the partition bin is part of a sequence of minimally L bins with a negative Z-score
  Neutral: otherwise A GipSeq-metrics-profile can be either a GipSeq-count-profile or a GipSeq-burden-profile. In the case of GipSeq-count-profiles, increases and decreases are interpreted as gains and losses respectively, for GipSeq-burden-profiles, they are assumed to represent burden rises and falls.

We use L=200 as the minimal length (in number of partition bins) of constant Z-score signs. In combination with a 10 kb bin size this means we target deviations of minimally 2 Mb.

The bottom row in FIGS. 2, 3, 13, 14 shows the GipSeq-metric-profile with L=3 as a minimum length for constant sign segments. Increases, decreases, and neutral bins are shown in light grey, dark grey and white respectively. Notice for instance in FIG. 2, that bins 1, 5, and 6 are neutral, bins 2 to 4 constitute a loss and bins 7 to 10 a gain.

To the extent the GipSeq-metrics-profiles of two GipSeq-clusters correspond to real imbalances observed in those clusters, we can express the similarity between their genome wide imbalance profiles in terms of the distance between their GipSeq-metrics-profiles. We here dene two distance scores based on the GipSeq-metrics-S-profile and GipSeq-metrics-P-profile respectively.

The S-distance between two GipSeq-metrics-S-profiles is the fraction of counted partition bins that mismatch. Counted bins are those that remain after removal of the bins that are neutral in both GipSeq-profiles. Mismatching bins are those that have non-identical values in both GipSeq-S-profiles, i.e. that are neither both increase nor both decrease.

Notice that the S-distance between each GipSeq-metrics-S-profile and itself is zero, and that the S-distance metric is symmetrical.

As an example, consider the two 12-bin GipSeq-metrics-S-profiles in FIG. 4, again with minimum length of increases and decreases L=3. The first and sixth bins are ignored as they are neutral in both GipSeq-metrics-profiles. This leaves 10 bins that are counted. Of those 10 bins, only bins 3, 4, 8, and 9 have identical values. So 6 out of 10 bins are mismatching, which translates to an S-distance of 60%.

The P-distance between two GipSeq-metrics-P-profiles is the Euclidean distance between the GipSeq-metrics-P-profiles of the partition bins. Let p,q be two GipSeq-metrics-P-profiles defined on n partition bins, then $$P\text{-distance}(p, q) = \sqrt{\sum_{i=1}^{n} (q_i - p_i)^2}$$

For GipSeq-metrics-S-profiles we introduce a custom discrete distance function to concentrate the calculation on larger constant sign segments. For GipSeq-metrics-P-profiles it is assumed this type of smoothing is inherent in the calculation of the percentile rank scores for the windows. As a consequence, a common off-the-shelf continuous metric such as Euclidean distance is applicable.

Analysis Tasks and Pipelines

With the above concept definitions in place, we are equipped to describe four closely intertwined analysis tasks:
  Detection of regional copy number (CNA) and mutation burden aberrations (MBA) via comparison of the GipSeq-metrics of a sample to the GipSeq-metrics in a reference set; these aberrations manifest themselves as peaks and valleys in the GipSeq-Z,L2R, and P-profiles
  Construction of GipSeq-clusters based on the S- or P-distance functions defined for GipSeq-Z-profiles and GipSeq-P-profiles respectively
  Annotation of samples as we can expect sample properties that are frequently observed in a GipSeq-cluster to carry over to samples in the GipSeq-cluster for which those properties are unknown
  Improvement of the sensitivity and specificity of CNA and MBA detection by adjusting or rebuilding the reference set dynamically in function of the sample or the ROI.

Detection of Regional Copy Number and Mutation Burden Aberrations

To call aberrations in a sample's GipSeq-metrics, thresholds on the GipSeq-profiles are required. For instance, a common choice for GipSeq-count-Z-profiles is to associate values Z≥3 to gains and values Z≤−3 to losses. In other words, for a copy number gain in a sample to be detected, its GipSeq-count should top the reference's GipSeq-count-mean by at least three times the reference's GipSeq-count-SD.

Consequently, two critical factors limit the detection of copy number aberrations (CNAs):

The concentration of the CNA in the sample: this could be less than 100% due to mosaicism and/or the fact that the cfDNA is a mixture (e.g., foetal, maternal, tumour, . . . )

The GipSeq-count of the reference set: with the same reference mean a larger reference SD will result in Z values closer to 0 and thus in more undetected CNAs The following derivation clarifies the link between these factors, for a duplication:

$$Zdup \geq 3 \Leftrightarrow \frac{count_{sample} - mean_{reference}}{SD_{reference}} \geq 3 \Leftrightarrow$$

$$\frac{mean_{reference} * (1 + 0.5 * concentration_{duplication}) - mean_{reference}}{SD_{reference}} \geq 3 \Leftrightarrow$$

$$0.5 * concentration_{duplication} * mean_{reference} \geq 3 * SD_{reference} \Leftrightarrow$$

$$concentration_{duplication} \geq 6 * \frac{SD_{reference}}{mean_{reference}} \Leftrightarrow$$

$$concentration_{duplication} \geq 6 * CV_{reference}$$

where CV is the coefficient of variation. Thus, CNAs can only be detected if their concentration exceeds six times the coefficient of variation of the GipSeq-count of the reference set. This suggests two remedies for improving CNA detection: somehow boosting their concentration in the sample, or switching to a reference set with a lower CV in the corresponding ROI bin. We return to the second option below.

Figure 15:
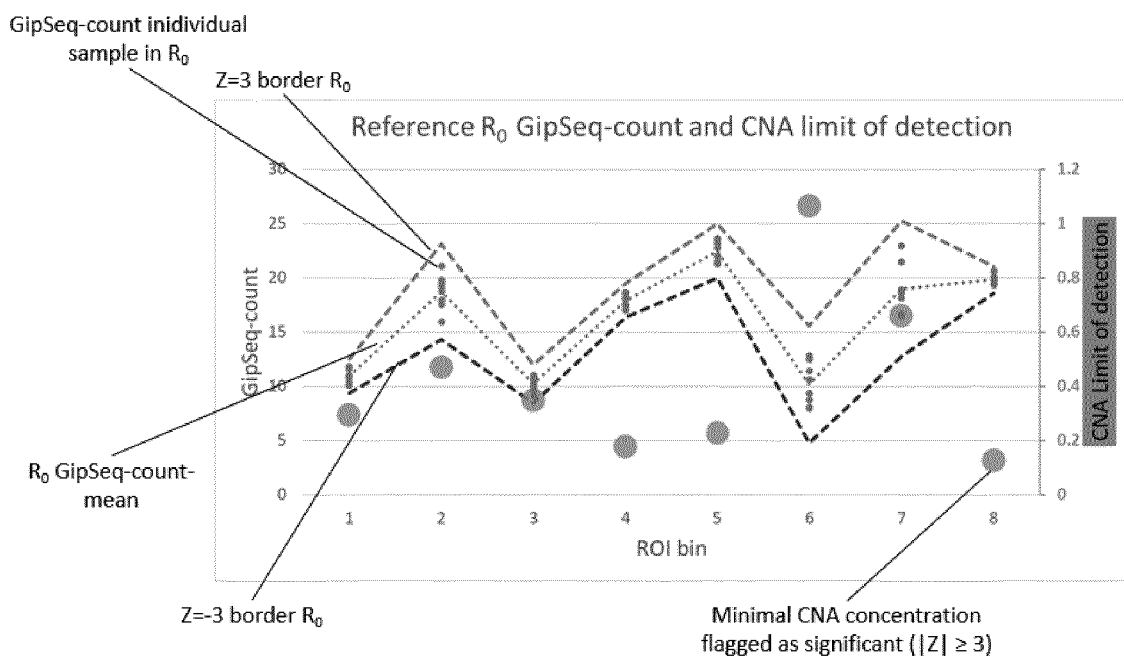
FIG. 15: Reference cluster borders and limit of detection. Small dots represent individual samples in reference set R0. The dotted line in the middle connects the mean per bin and the dashed lines represent the Z=3 borders. The large dots mark per bin the CNA limit of detection w.r.t. the right Y-axis.

FIG. 15 further illustrates the relationship between the reference GipSeq-count-CV and CNA concentration for eight ROI bins. Notice for instance that the reference R0 GipSeq-count (left Y-axis) varies less in ROI bin 1 than in ROI bin 2. Consequently, in bin 2 the upper and lower borders (plotted as dashed lines) for |Z|=3 are further apart and the 6*CV limit of detection (LOD) (large dots, right Y-axis) for CNAs is higher than in bin 1. Notice also that CNAs in bin 6 are not detectable with reference $R_0$, since their limit of detection exceeds 100% concentration.

Figure 16:
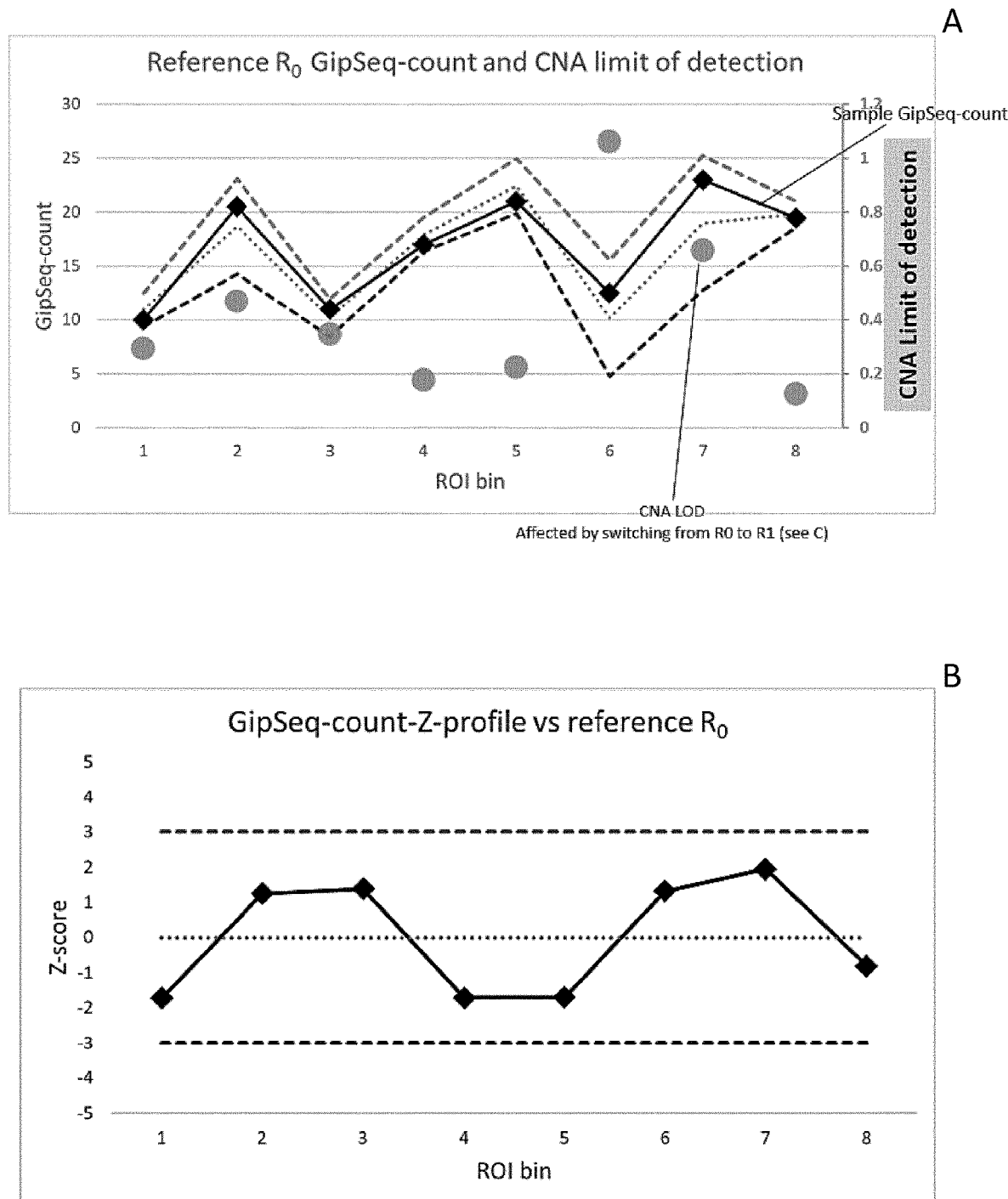
FIG. 16: Sample with reference cluster borders and limit of detection. A-B: reference R0 where any CNAs in the sample go undetected. C-D: adjusted reference R1 reveals CNA in bin 7.
Figure 16:
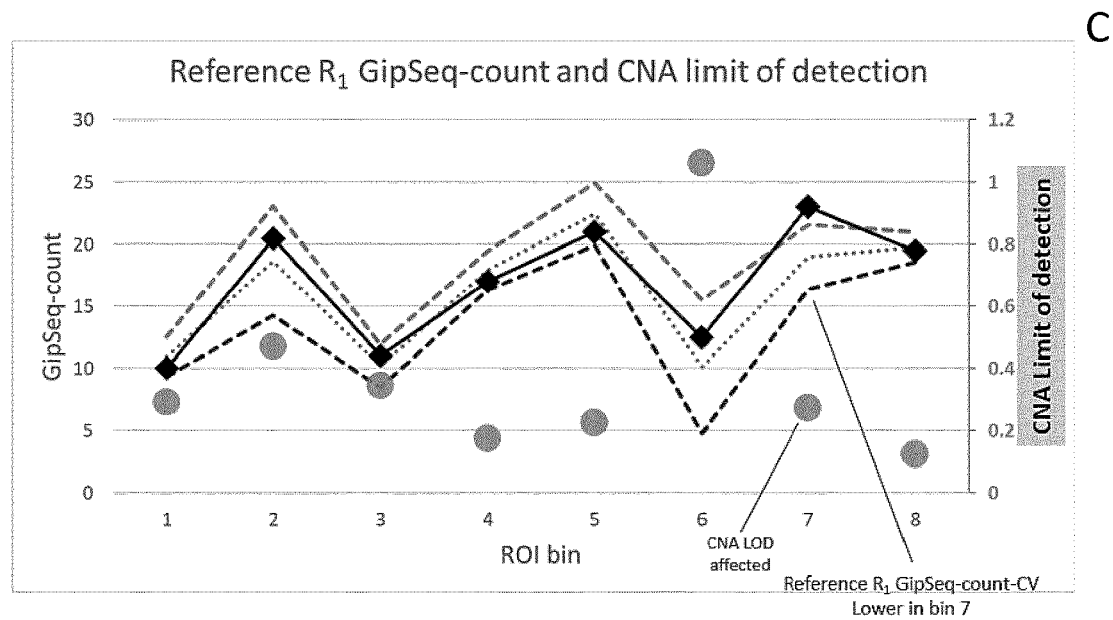
Figure 16:
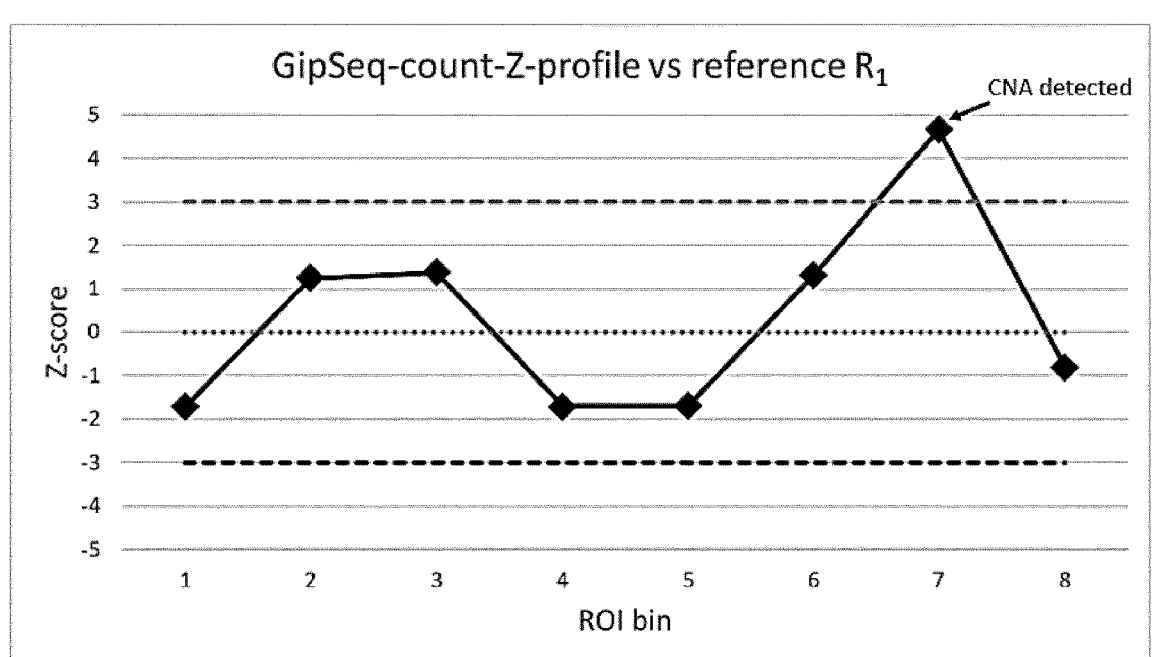

The chart in FIG. 16.A shows a sample that is seemingly CNA free. More correctly, it does not contain any CNAs in ROI bins 1-8 at a concentration where they can be picked up with reference $R_0$. This can also be observed in the GipSeq-count-Z-profile FIG. 16.B, where the Z-score for all ROI bins falls inside the |3,3| interval. FIG. 16.C-D illustrates how a change in the reference set affecting ROI bin 7 lowers the limit of detection for that bin from 66% to 27%, in this case revealing the presence of a duplication.

Construction of GipSeq-Clusters and Sample Annotation

The S and P distance functions allow us to group sequenced samples using any unsupervised clustering algorithm. To describe the construction of GipSeq-clusters and its interaction with sample annotation, we have adopted the Leader algorithm [J. A. Hartigan. Clustering Algorithms, 1975]. The steps discussed below are all illustrated in FIG. 17.

Figure 17:
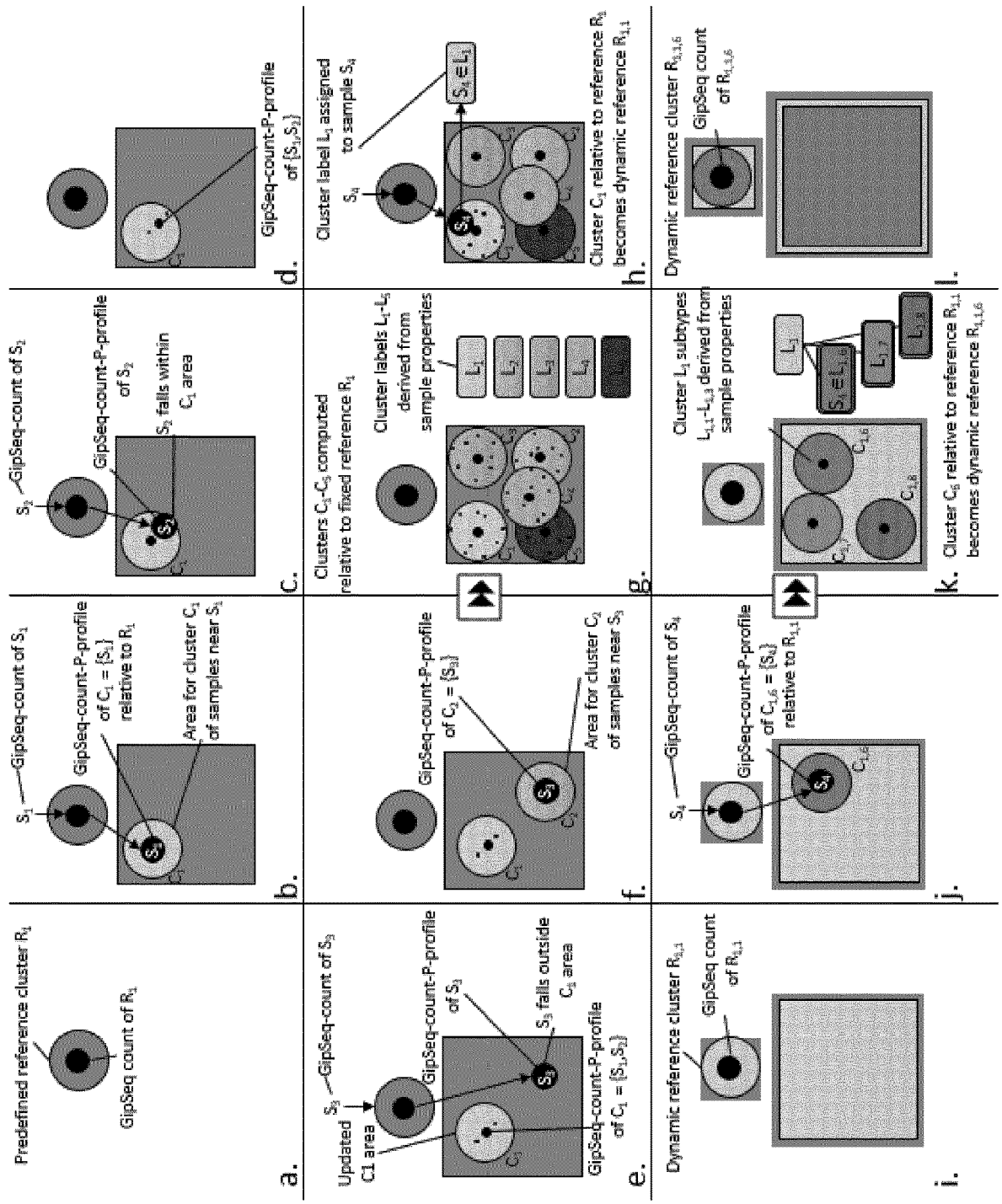
FIG. 17: The GipSeq-flow: iterative construction of GipSeq-clusters, sample annotations, and dynamic reference sets

FIG. 17.a: Initialization

The starting point is a predefined reference cluster $R_1$. For this set we would typically use at least 100 sequence samples of "good quality" that are considered to be (1) maximally close to normal and (2) representative of the sample types we expect in the future. As discussed above, the $R_1$ GipSeq-count determines the CNA limit of detection for each of the bins.

FIG. 17.b: Adding a First Sample

The first sample S1 is compared to R1 and its GipSeq-P-count profile becomes the GipSeq-P-count-profile of a new cluster $C_1$. The dark grey square represents the Euclidean space of GipSeq-count-P profiles computed using $R_1$ as a reference. The light grey circle delineates a zone of GipSeq-count-P-profiles whose P-distance to $C_1$ is below a predefined threshold T. Sample $S_1$ is now the leader of $C_1$. Alternative names would be centroid or prototype.

FIG. 17.c: Adding a Second Sample

For the second sample $S_2$ we calculate the P-distance between the GipSeq-count-P-profiles of $S_2$ and $C_1$. It turns out this distance is smaller than our predefined radius T, so $S_2$ is added to $C_1$.

FIG. 17.d-e: Updating the Cluster

With cluster $C_1=\{S_1,S_2\}$ the GipSeq-cluster-P-profile of $C_1$ has to be recomputed. This new profile no longer corresponds to an existing sample, but can be seen as virtual leader at the centre of the adjusted light grey circle representing $C_1$.

FIG. 17.e-f: Adding a Third Sample

Figure 9:
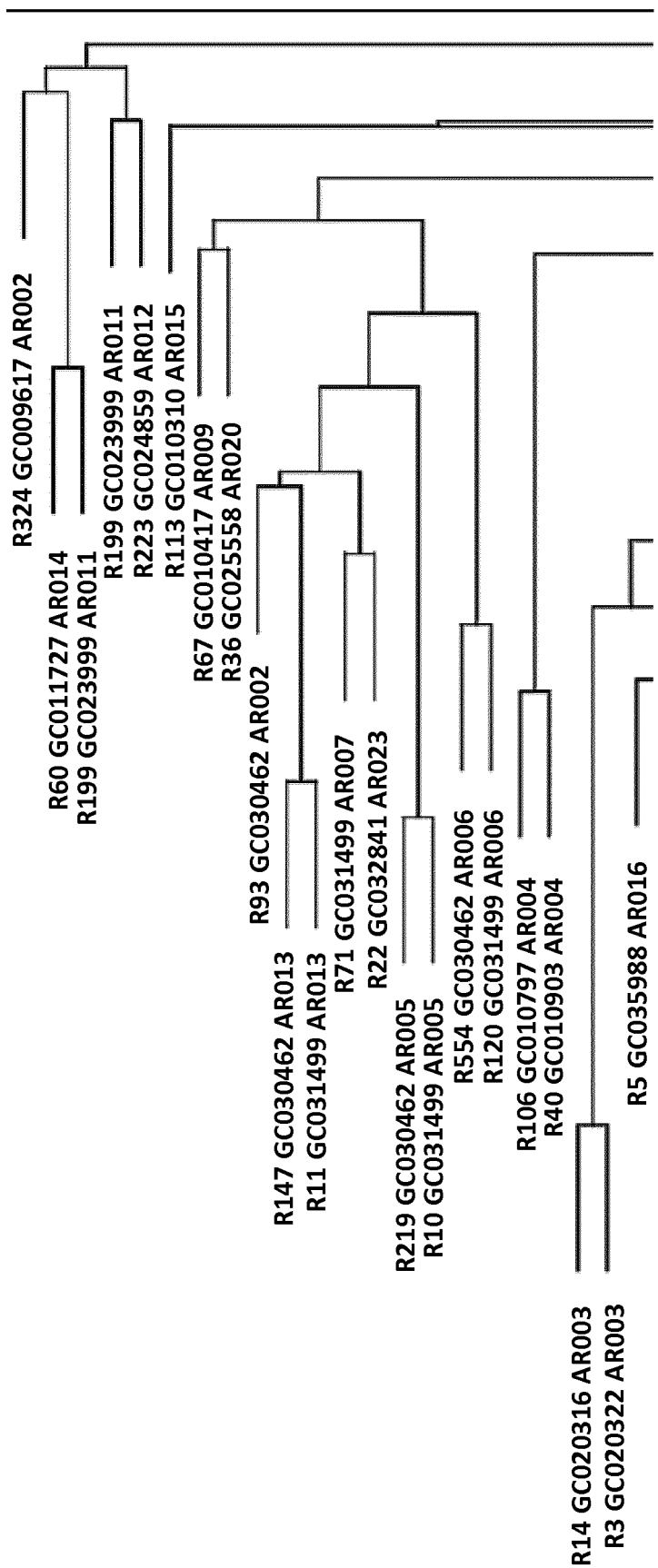
FIG. 9: GipSeq-cluster with samples similar to the lupus case highlighted.
Figure 9:
Figure 10:
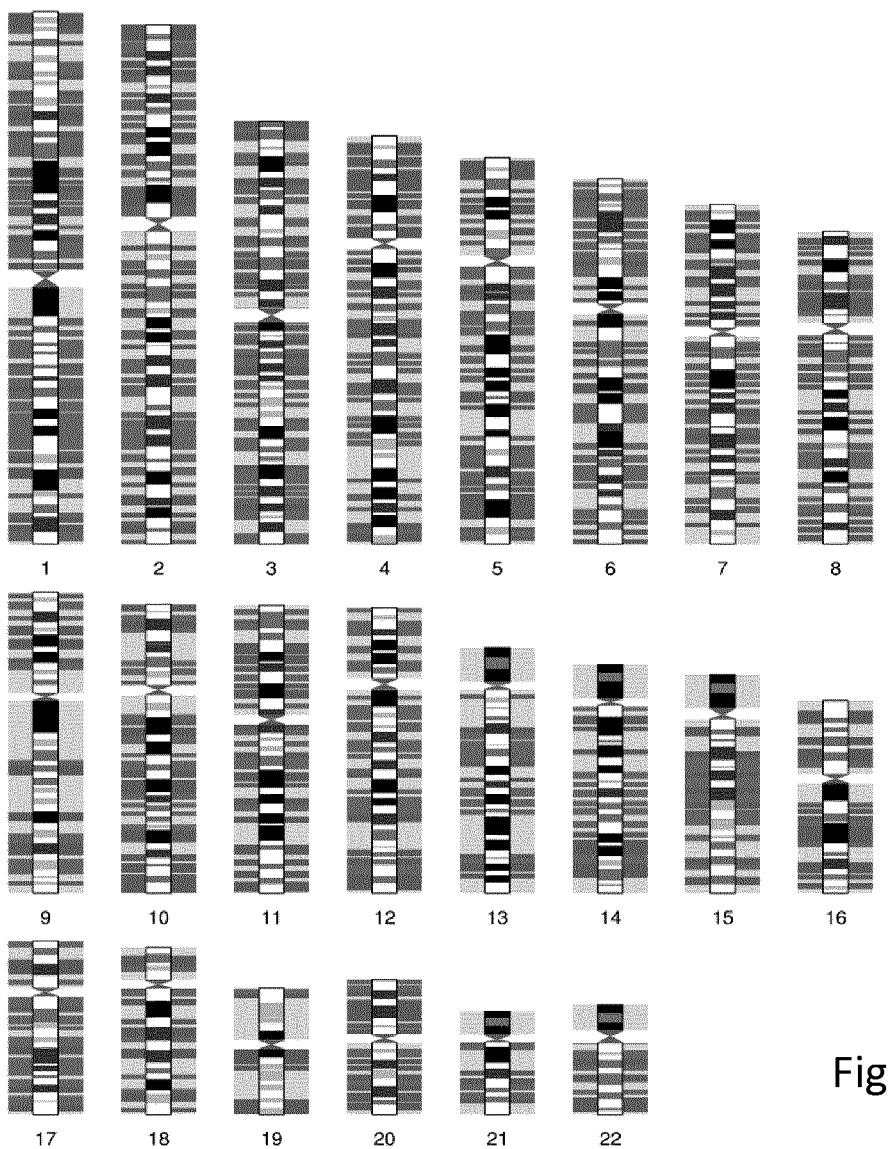
FIG. 10: GipSeq-profile of lupus related samples.

The P-distance between sample $S_3$ and $C_1$ exceeds radius T, so, similar to $S_1$ in step FIG. 9.b, $S_3$ gives rise to a new cluster $C_2$. Future samples will have to be compared to both $C_1$ and $C_2$.

FIG. 17.g: Clustering Result

As more samples are added the number of clusters grows. The total number of clusters is to a large extent determined by the predefined cluster radius T. We aim at a choice for T that results in a number of clusters that approximates the square root of the total number of samples (e.g., for 50000 samples 223 clusters). Notice GipSeq-clusters are allowed to overlap, as newly arriving samples are added to all clusters to which they are near.

FIG. 17.g-h: Sample Annotation

In case the clustered samples have been annotated, e.g., with disease labels, lists can be drawn of labels that are frequently associated to that cluster. In doing so, we are linking the GipSeq-cluster-P-profile of a cluster to sample properties. New samples with a similar GipSeq-cluster-P-profile can then be assumed to share those properties.

Improving Sensitivity and Specificity of CNA and MBA Detection

The reference set adjustment illustrated in FIG. 16.C-D aims at improving the sensitivity of CNA and MBA detection in a particular bin. In this section we will describe more generally how a reference set can be optimized dynamically either by fixing an existing one or by building one from scratch tailored to a particular sample.

To fix an existing reference we can try to eliminate some of its variability. Two strategies can be distinguished:

Excluding samples. This strategy applies in case the variability in a bin is mainly due to a couple of samples whose removal leaves the GipSeq-count of other bins largely intact. In particular, removal of samples from the reference set that have a CNA that spans a particular bin will improve the bin's CNA-LOD.

Blacklisting regions, i.e., ignoring genomic intervals during computation of the GipSeq-counts. This strategy is appropriate for large ROI bins (e.g., full chromosomes) that contain relatively small but highly variable subregions (e.g., centromeres). To implement it, we can rank 10 kb subregions of the ROI bin by SD. The top of this ranking can then be appended to the blacklist until the targeted sensitivity is obtained, or until the blacklist has reached its maximal size beyond which the remaining GipSeq-counts no longer represent the whole bin.

The concept of improving the sensitivity by editing the reference set is illustrated above in FIG. 16, where modification of $R_0$ (charts A,B) to $R_1$ (charts C,D) corrects a false negative CNA call in bin 7.

Rebuilding

Figure 18:
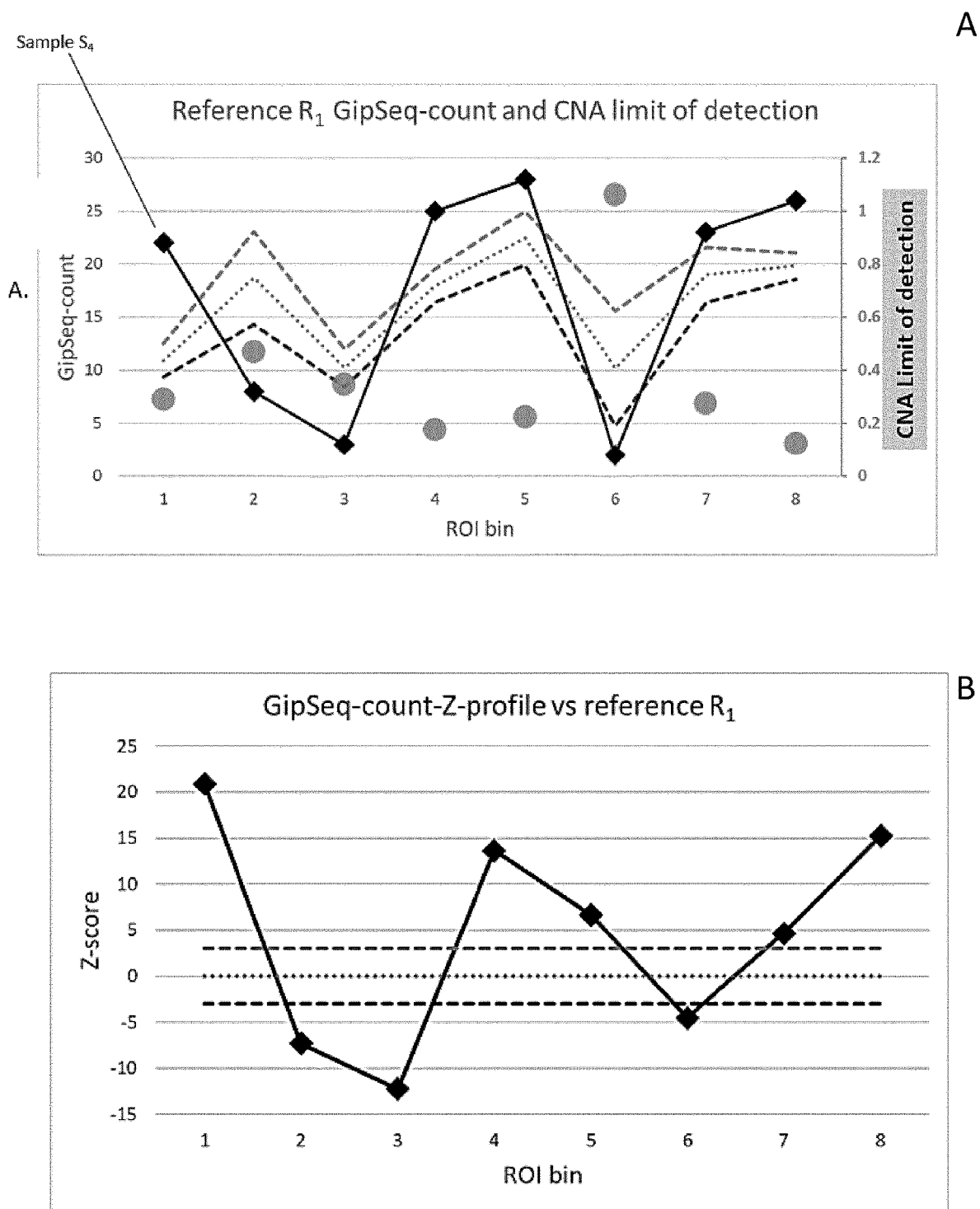
FIG. 18: Reanalysis of sample S4 that is aberrant when compared to R1 (see charts A,B). When compared to dynamically constructed R1,1 (see charts C-E), both specificity (e.g., bin 7) and sensitivity (bin 3) rise.
Figure 18:
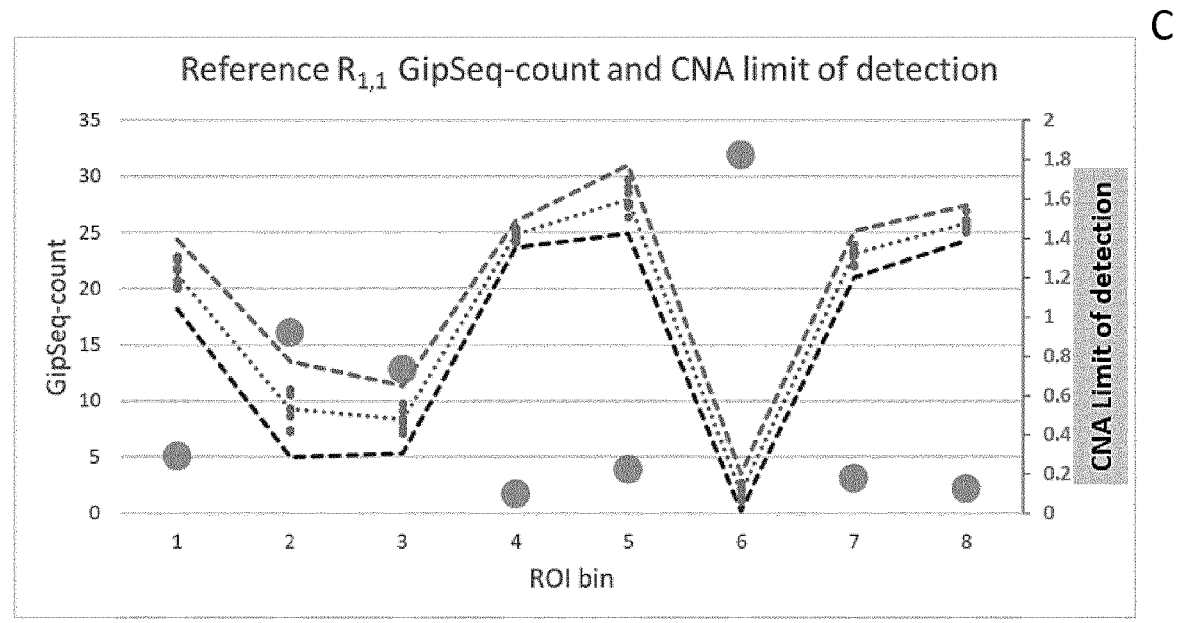
Figure 18:
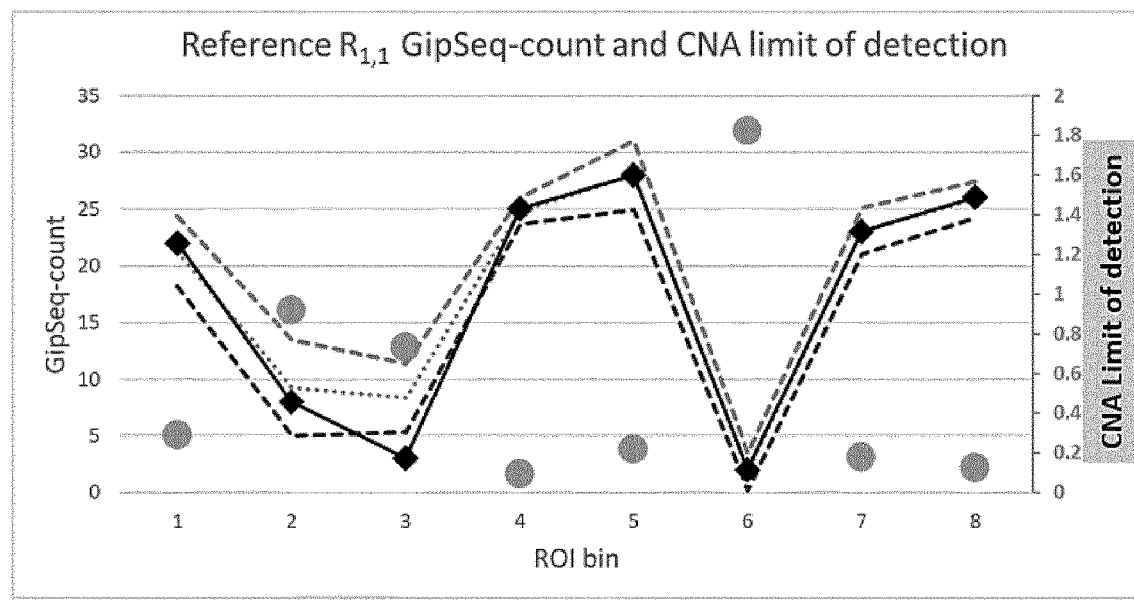
Figure 18:
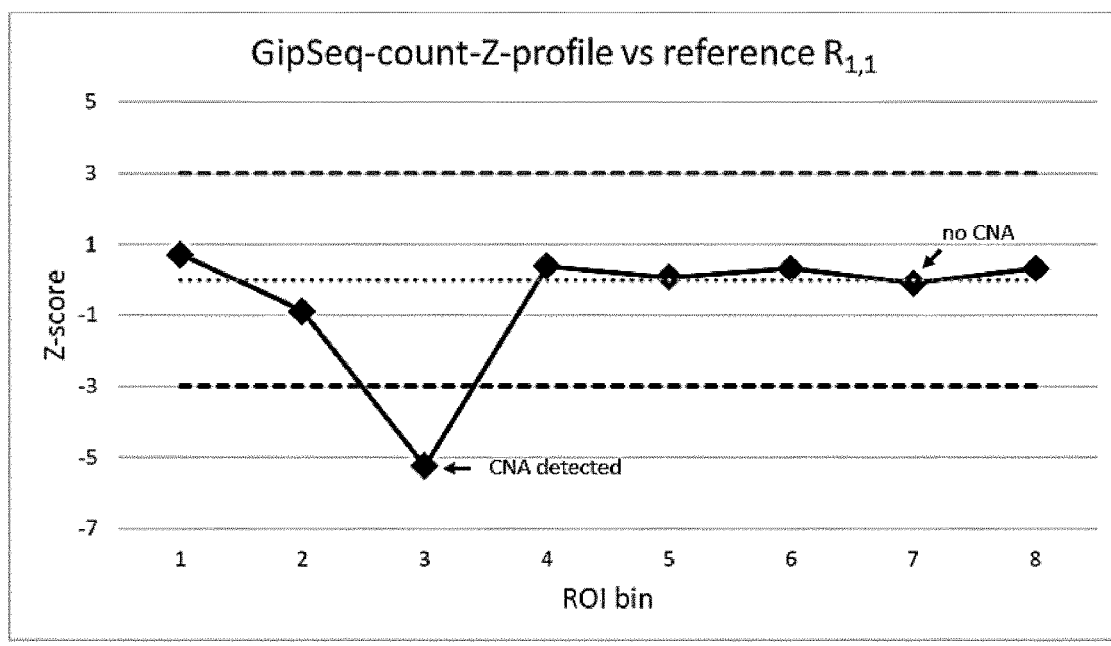

Consider chart FIG. 18.A which shows a sample $S_4$ compared to the same reference $R_1$ as used in FIG. 16.B. The sample GipSeq-count for bin 7 is identical and aberrant in both charts. Notice however that where bin 7 is the exception in FIG. 16.C-D, it is not in FIG. 18.A where the GipSeq-counts for all bins of $S_4$ are aberrant. FIG. 18.B further illustrates this point: the Z-profile of $S_4$ compared to $R_1$ is outside the |−3,3| interval for all bins. This suggests the aberrations are not caused by CNAs, but rather by a more radical factor creating genome wide imbalances and impacting all GipSeq-counts of $S_4$. In case this same factor has been encountered in previous analyses we would be in the situation depicted in FIG. 17.*h*, where these cases are clustered in $C_1$, and sample $S_4$ is assigned to $C_1$ based on the small P-distance between the GipSeq-count-P-profiles of $S_4$ and $C_1$. A new reference set tailored to $S_4$ can then be created as outlined in FIG. 17.*h-k*.

FIG. 17.*h* For the creation of a reference set tailored to $S_4$ we want to retrieve samples from our historical collection with a genomic imbalance profile that is similar to $S_4$. With rapidly growing historical collections calculating the P-distance between each new sample and all samples analysed in the past quickly becomes impractical. For this purpose, the clusters illustrated in FIG. 17.*g-h* serve as an index. It then suffices to calculate the distance between $S_4$ and all the (virtual) cluster leaders. The collection of samples associated with the nearest cluster leader—$C_1$ in the example—can then be promoted to a new reference set $R_{1,1}$, optionally optimized with the fixing strategies described above.

Alternatively, the $C_1$ samples can be ranked by P-distance to $S_4$, most similar samples on top. A roll down through this ranking can then be implemented where the quality of reference set is monitored as more samples are added. Two key properties should be verified at each step to maximize the effectiveness of the new reference:

1. In the interest of specificity, the reference set should be similar to sample $S_4$. This should be guaranteed since we draw from $C_1$ most similar samples first.

2. In the interest of sensitivity, the variation in the reference should be checked, in order to minimize the LOD for each of the bins. We can then stop growing the reference set as soon as there is a jump in the LOD of critical bins.

FIG. 17.*i* As suggested in the drawing and the naming, reference cluster $R_{1,1}$ is created in the context of $R_1$, nested inside $R_1$: the GipSeq-count of $R_{1,1}$ is calculated from samples that look similar when their GipSeq-counts are compared to those of $R_1$.

FIG. 17.*j* A new GipSeq-count-P-profile for $S_4$ can be calculated based on the comparison with the GipSeq-count of $R_{1,1}$. As in FIG. 21.*b*, this results in a new cluster $C_{1,6}$ with $S_4$ as leader.

FIG. 17.*k* As more $C_1$ samples are analysed with $R_{1,1}$ subclusters $C_{1,6}$-$C_{1,8}$ emerge. Common properties found in those subclusters result in subtypes $L_{1,6}$-$L_{1,8}$ of $L_1$. So, in addition to annotation $L_1$ acquired via its membership of $C_1$, sample $S_4$ is subtyped as $L_{1,6}$ via its similarity to the $C_{1,6}$ leader.

FIG. 17.*l* The concept of dynamic reference creation can be applied iteratively to create layers of reference sets, subclusters, and sample labels of arbitrary depth. For instance, the analysis of samples sorted to $C_1$ with reference $R_1$ and to $C_{1,6}$ with reference $R_{1,1}$ can be further renewed by comparing them to reference $R_{1,1,6}$ based on $C_{1,6}$.

To conclude, the impact of reanalysing samples with a dynamically constructed and tailored reference set is twofold:

Improved sensitivity: since the reference set contains samples similar to each other, the reference GipSeq-count-CV is expected to drop, leading to an LOD drop in all bins and more CNAs and MBAs detected Improved specificity: since the reference contains samples that have a genomic imbalance profile that is similar to the analysed sample, any remaining regional aberrations are more likely to be genuine.

These effects are further illustrated in FIG. 18. The chart in FIG. 18.0 represents the new reference set $R_{1,1}$ from FIG. 18.*i* based on cluster $C_1$ of samples that are similar to $S_4$. In chart FIG. 18.D-E sample $S_4$ is compared to $R_{1,1}$ (cf. FIG. 17.*j*), which results in a more stable pattern. The false positive calls in bin 7 (and in 6 other bins) are corrected, exposing bin 3 as the exceptional—and therefore more likely—aberration.

Figure 11:
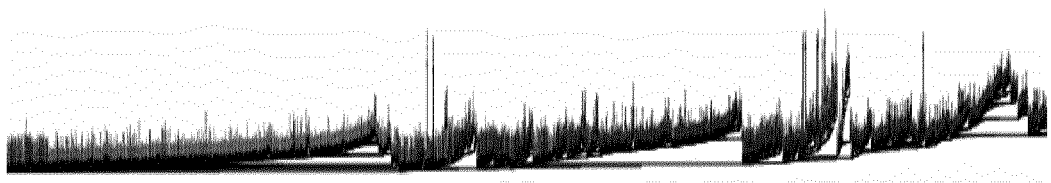
FIG. 11: GipSeq-cluster with Hamilton-processed samples indicated in light grey versus other samples in black.

The iterative nature of our proposed method for improving the efficiency of a reference set is visualized in FIG. 11. Boxes 1 to 12 (excluding boxes 6 and 11) represent the state-of-the-art procedure of generating reports on copy number aberrations (incl. trisomies) from sequencing data. To this common pipeline we have added two critical extensions.

1. Samples are annotated via the similarity of their GipSeq-metrics-profiles to samples of know class (box 14). Translated to the patient level this means:

patients are diagnosed with a known disease based on the GipSeq-metrics-profiles they share with patients proven to have the disease patients suffering from an unidentified disease are grouped together, and their shared GipSeq-metrics-pro le might contribute to our understanding and identification of the common phenotype 2. The loop in from box 10 to 17, where each analysis suggests a superior reference set for the next round, allows us to obtain progressively higher sensitivity and specificity at both the CNA/MBA detection and sample classification task.

Example 1—Cancer Diagnosis

We calculated the GipSeq-profiles of over 20000 sequenced samples, normalizing them against a randomly composed reference GipSeq-cluster of 1000 samples. From these GipSeq-profiles, we selected about 2500 with at least one of the following properties:

1. the GipSeq-profile contains at most ⅔ neutral regions, i.e., the sample contains at least ⅓ gains or losses as described in example 1.

2. the corresponding sample is submitted via a clinical study

Figure 5:
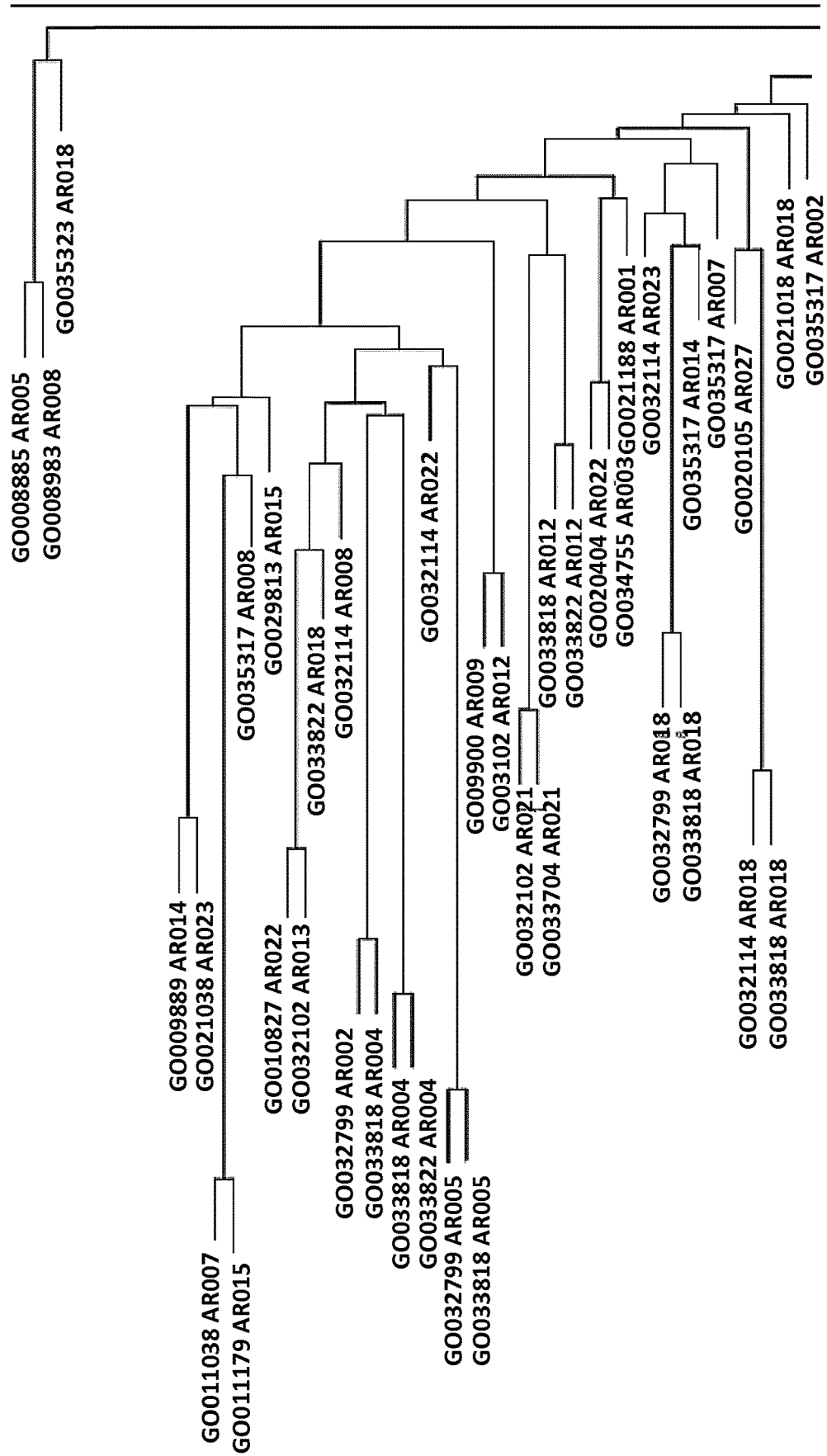
FIG. 5: Segment of a GipSeq-cluster containing tumor samples.
Figure 5:
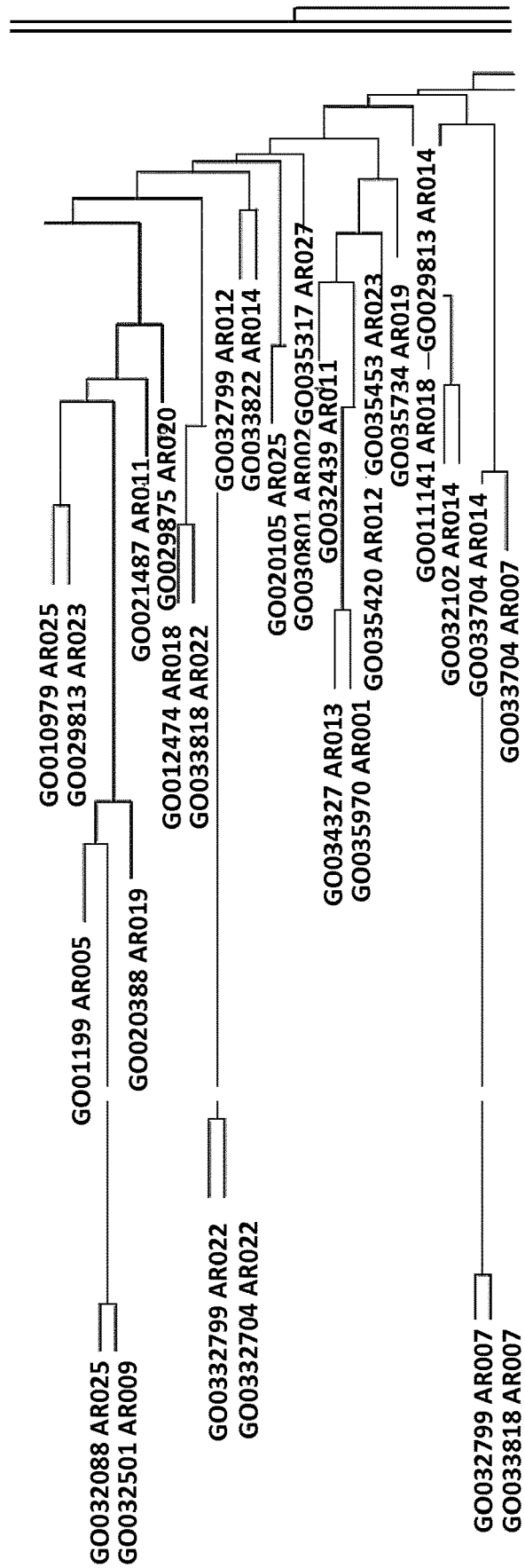

Next, we grouped the 2500 selected GipSeq-profiles into GipSeq-clusters by means of a hierarchical clustering method and the similarity metric described in example 1. FIG. 5 shows a segment of the resulting cluster tree. The samples in this segment are known to be associated to cancer (i.e. they are reference samples for cancer) and will further be referred to as tumour samples.

Figure 6:
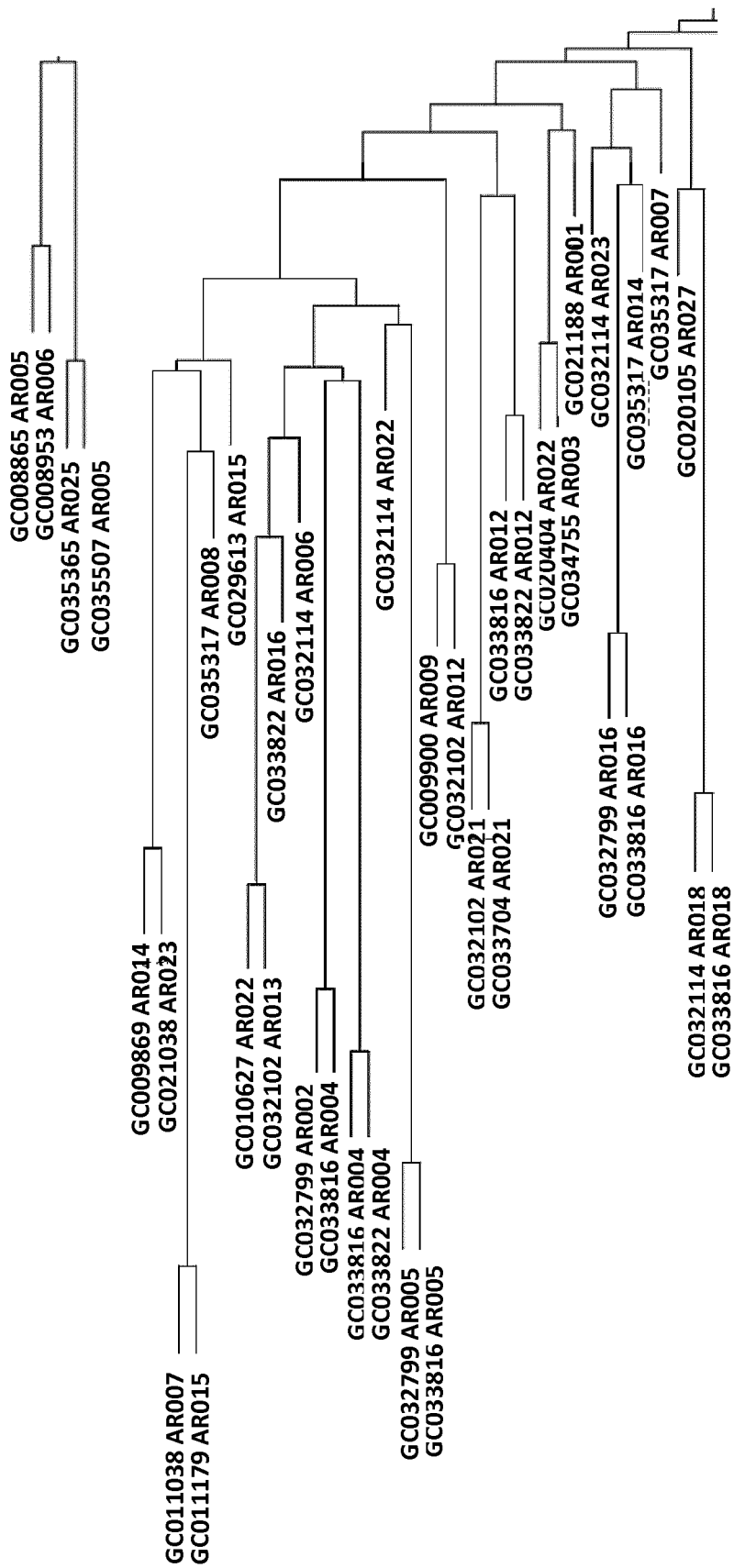
FIG. 6: GipSeq-cluster of FIG. 5 with addition of new samples.
Figure 6:
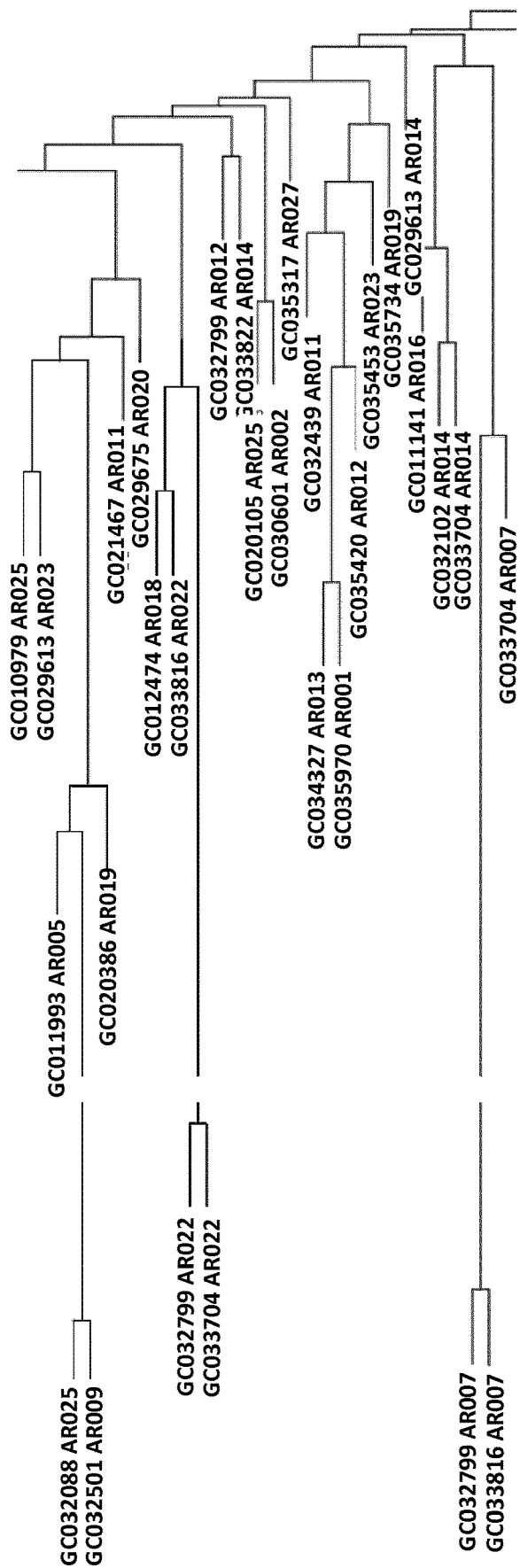

We then added a fresh batch of samples and repeated the clustering to verify if any new samples show affinity with phenotypes represented in the GipSeq-cluster. For the cancer phenotype, the result can be seen in FIG. 6, in which the two members of the new batch that cluster with the tumour samples are highlighted. These samples originate from the same patient.

Figure 7:
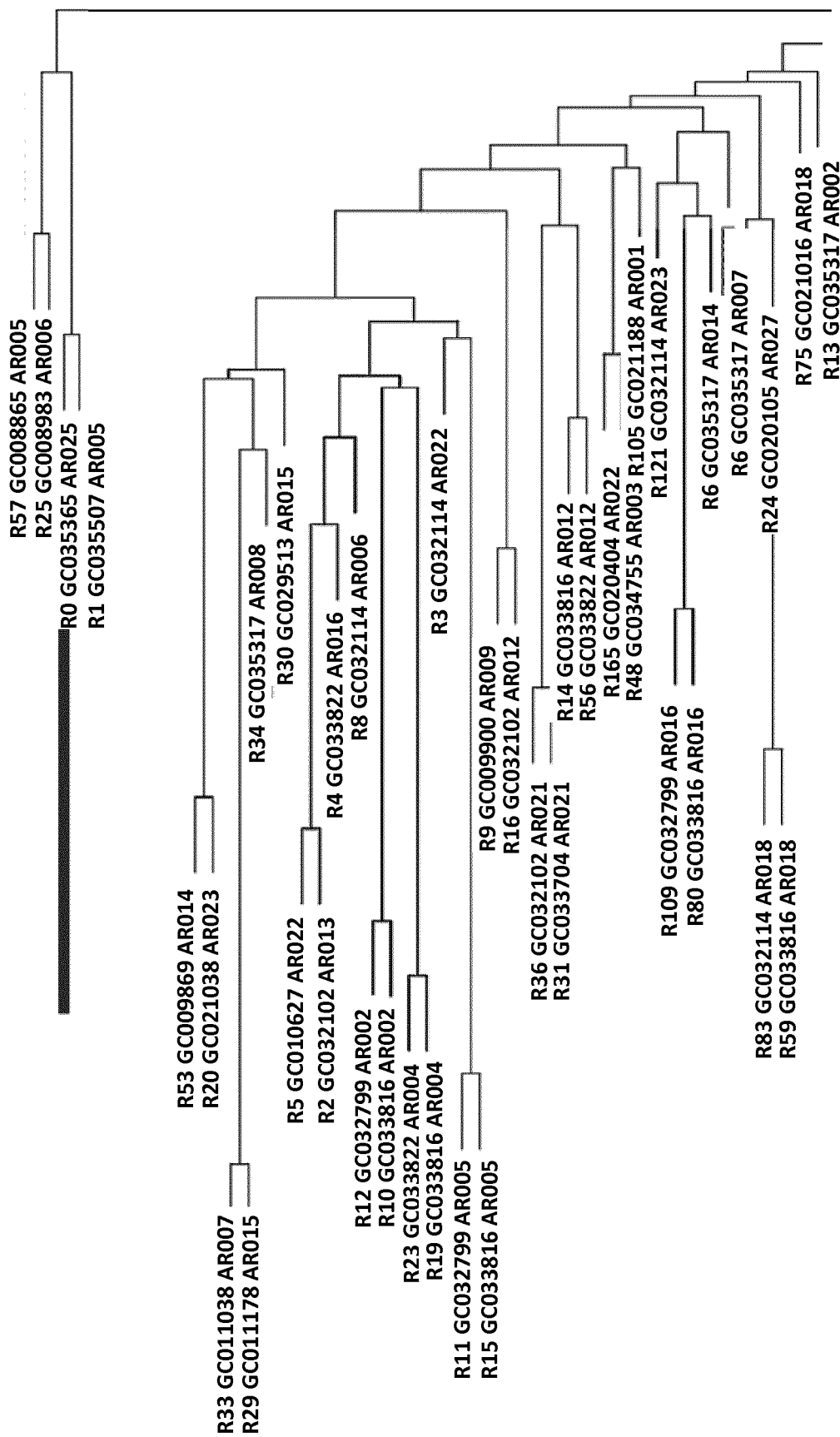
FIG. 7: GipSeq-cluster of FIG. 6 with grey-scale coding
Figure 7:
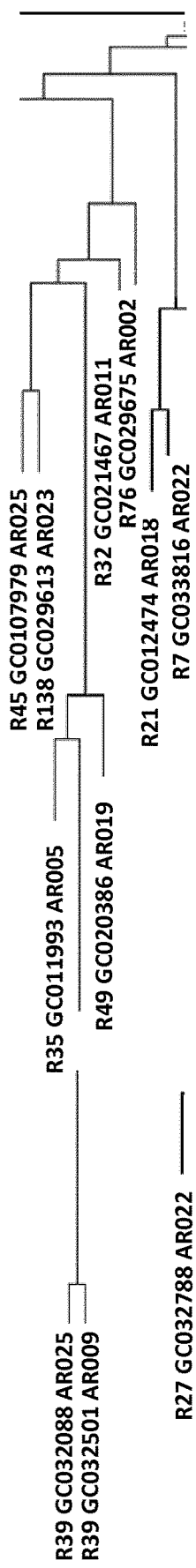

One of them, namely GC035365-AR035, is visualized in FIG. 7 using a color gradient, where the most similar samples are shown in dark grey, and the less similar ones in light grey. The Rx prefix in each label indicates the position in the similarity ranking. Notice the sample under investigation has label R0. As expected, the repeat sample from the same patient ranks first (R1). The most similar known tumour sample in the set is GC032102-AR013 and ranks second (R2).

Figure 8:
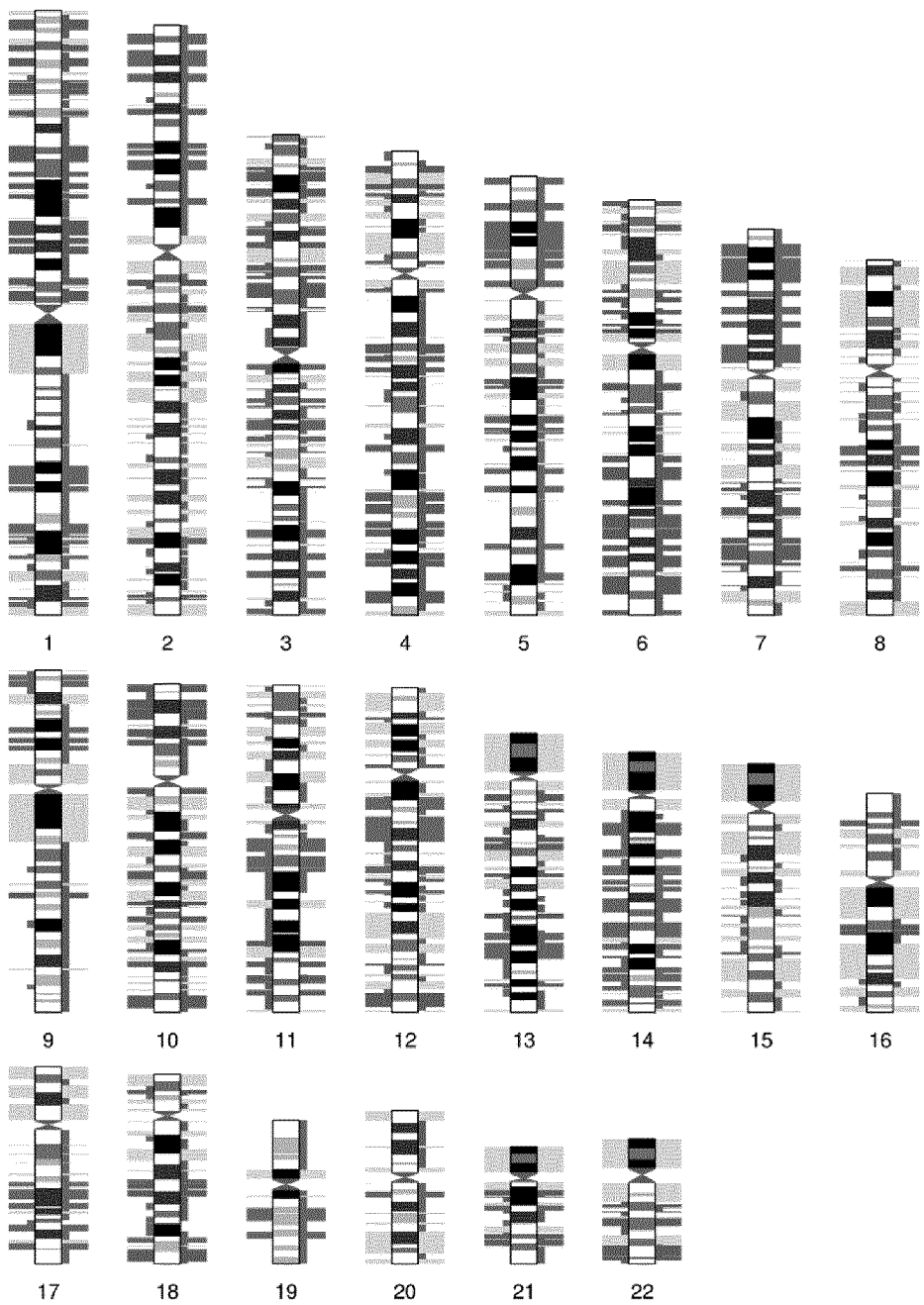
FIG. 8: Comparison between two GipSeq-profiles GC035365-AR025 (to the left of the chromosome) and GC03102-AR013 (to the right of the chromosome).

FIG. 8 shows the GipSeq-profile alignment of GC035365-AR035 (R0) vs. GC032102-AR013 (R2). The overall similarity between the two profiles is 29%. Regions marked in light grey are neutral in both samples and excluded for similarity calculations. As in FIG. 4 above, gains and losses are marked in darker grey. Long horizontal lines mark areas where both samples match. Regions where a gain or loss in one sample is not matched in the other sample are marked by a shortened horizontal line on one side only. For instance, chromosome 1 starts with a common neutral region (full light grey block), followed by an unmatched loss in GC032102-AR013 (dark grey stump to the right) and a common loss (dark grey block).

To summarize, our analysis of GC035365-AR025 in the context of about 2500 clustered samples produced the following evidence:
1. hierarchical clustering positions the sample next to a cluster of known tumour samples (FIG. 6)
2. analysis of a second sample from the same patient yields highly similar results (FIG. 6)
3. several known tumour samples rank on top in the list of most similar samples (FIG. 7)
4. a particular pattern of gains and losses (FIG. 8) is shared with a known tumour sample The combined evidence supports the classification of this case as a potential tumour sample. Effectively, the patient was referred to the clinic for follow up examinations and -presymptomatically-diagnosed with cancer.

Example 2—Lupus Diagnosis [1]

Samples GC038938-AR012, GC039015-AR012, and GC039500-AR009 showed a common distorted GipSeq-profile and all originated from a patient diagnosed with lupus. A similar GipSeq-profile has been observed in about 40 other samples, causing them to cluster together, as shown in FIG. 9. These other samples will be reviewed to confirm that they have been derived from other lupus patients or individuals with lupus related disorders i.e. autoimmune disorders).

Example 3—Lupus Diagnosis [2]

Figure 20:
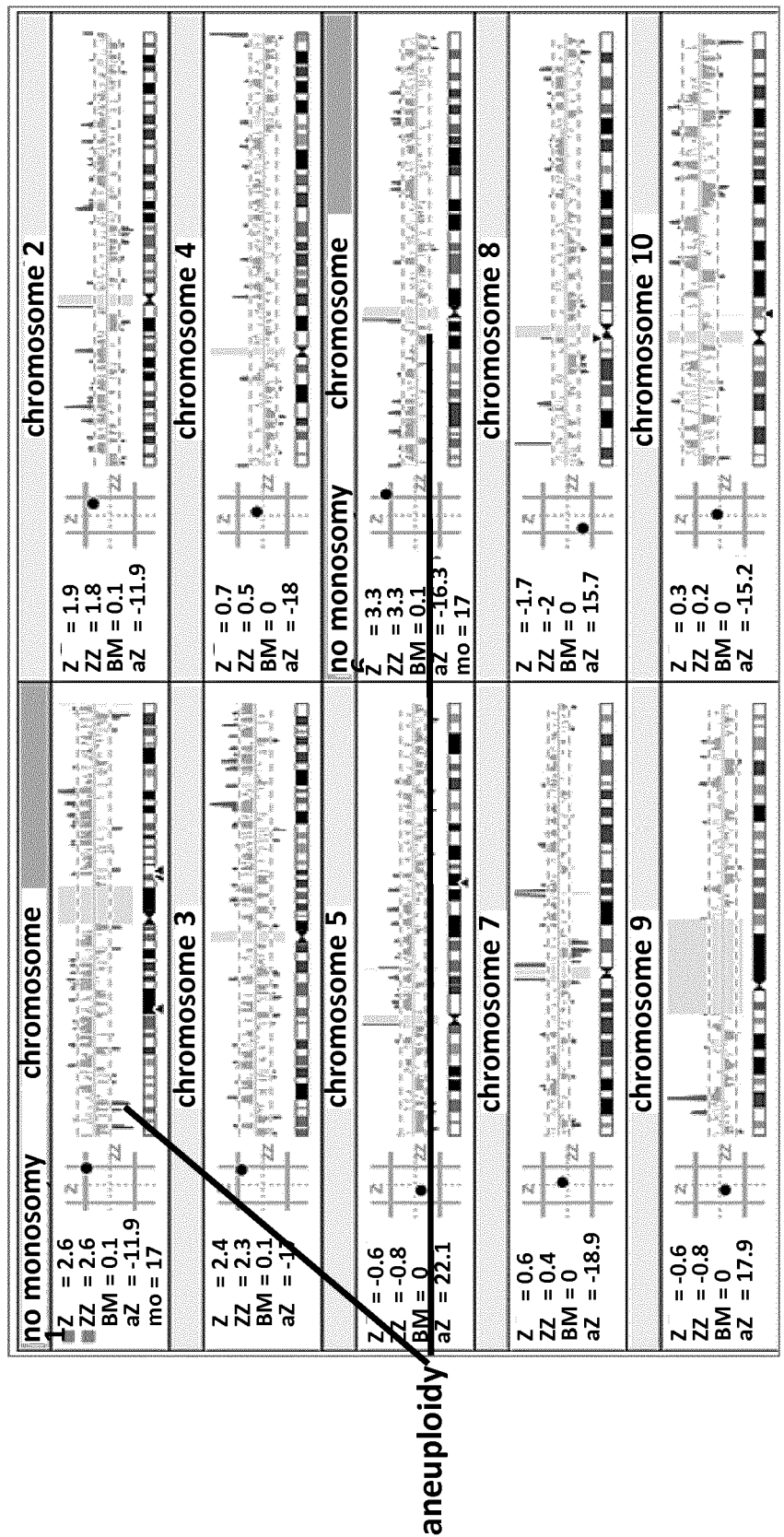
FIG. 20: Sample Lupus1 failing quality control when analysed with the initial reference set (left side), returns normal when analysed in the context of 40 similar samples.
Figure 20:
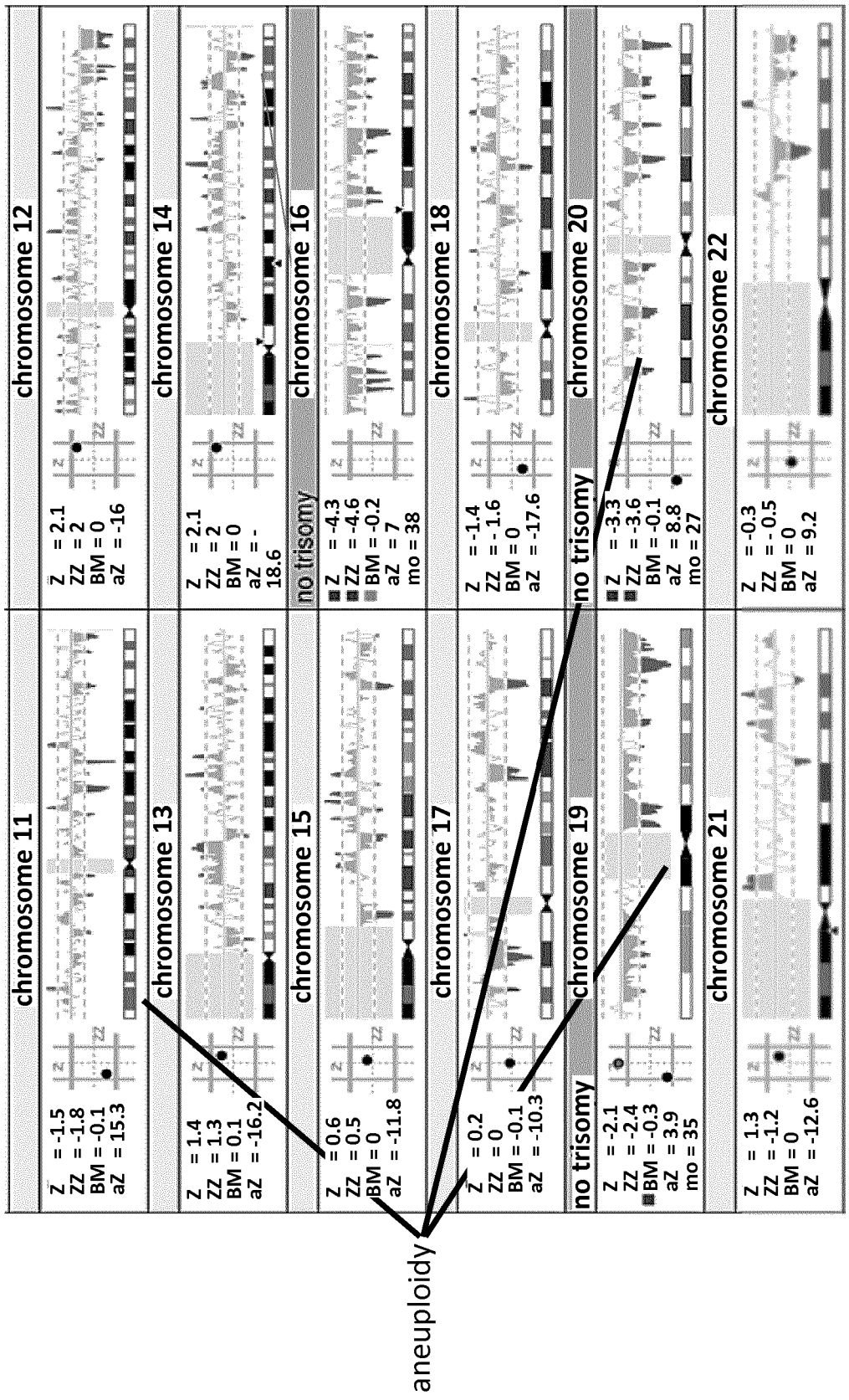
Figure 20:
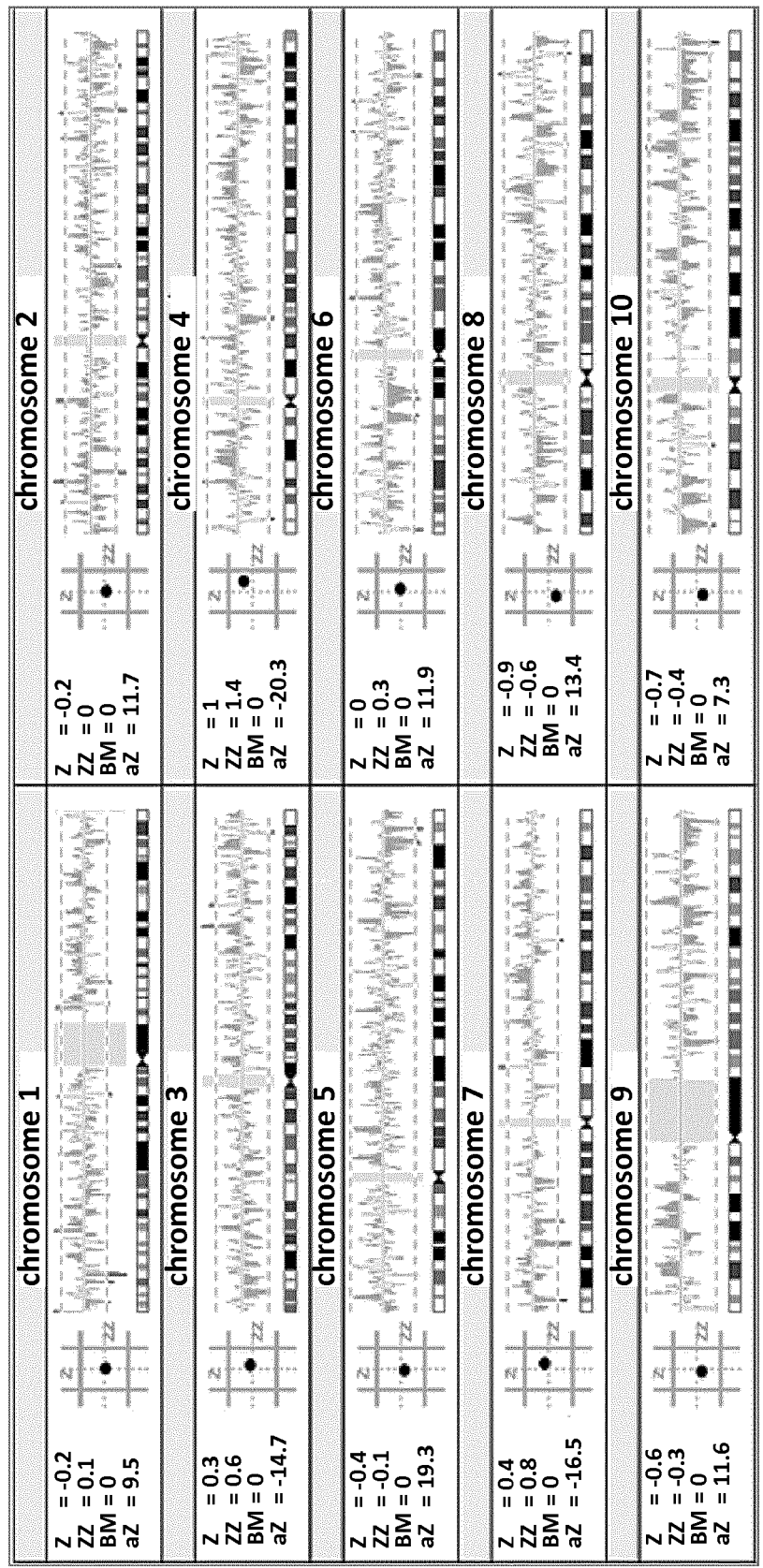
Figure 20:
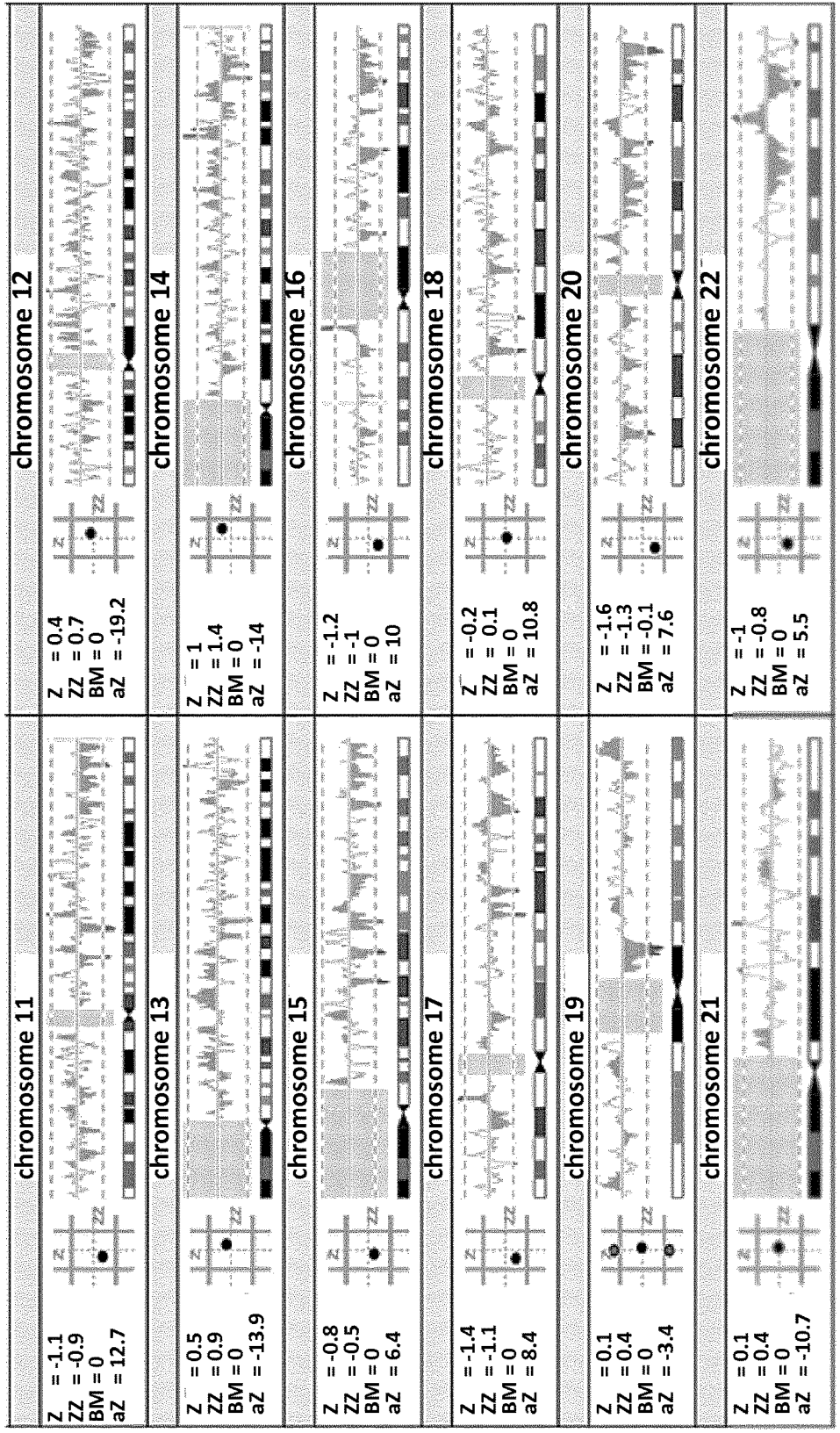
Figure 21:
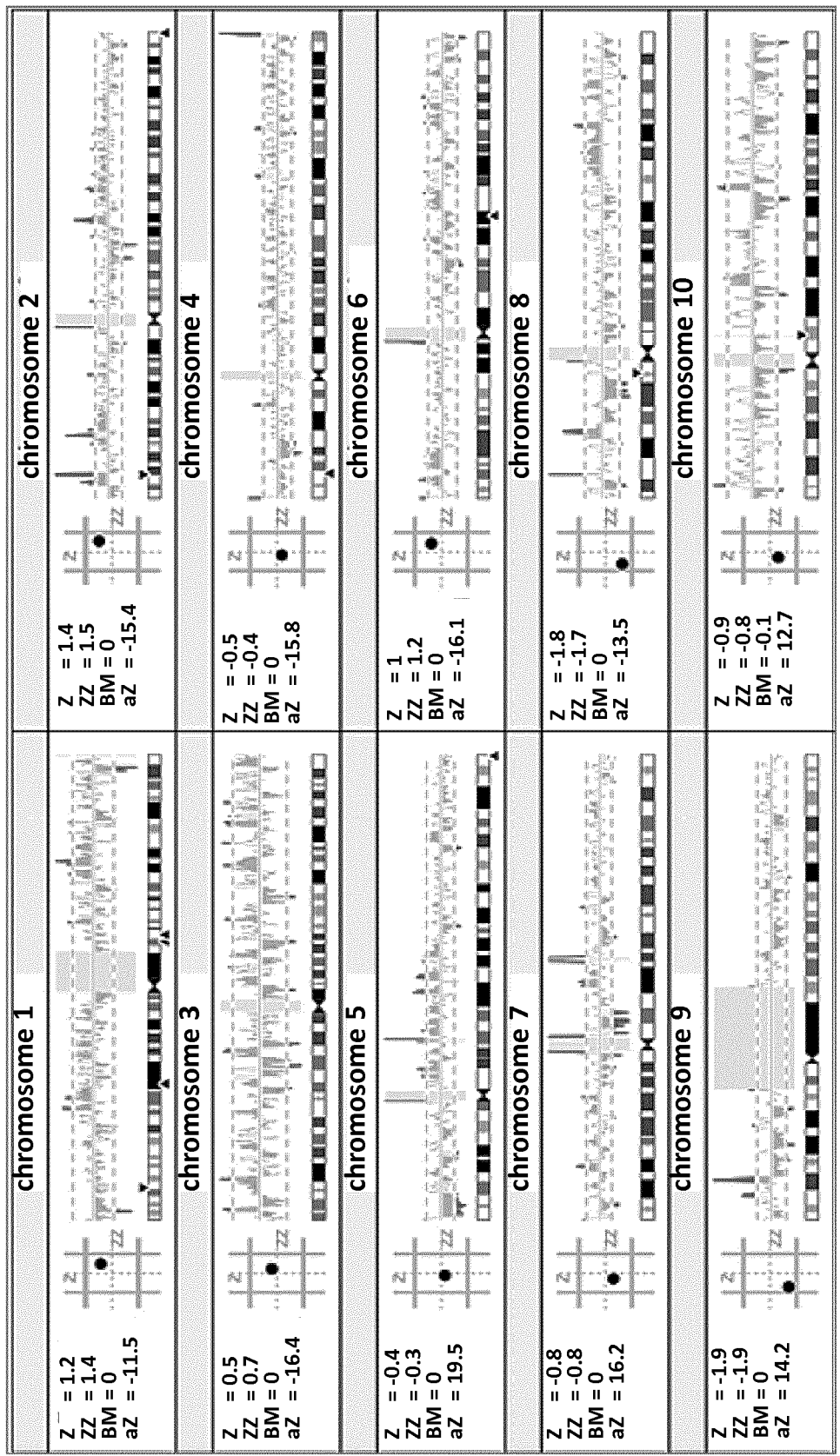
FIG. 21: Sample Lupus2 failing quality control when analysed with the initial reference set (left side), passes quality control when analysed in the context of 40 similar samples and is marked as containing a chromosome 18 trisomy.
Figure 21:
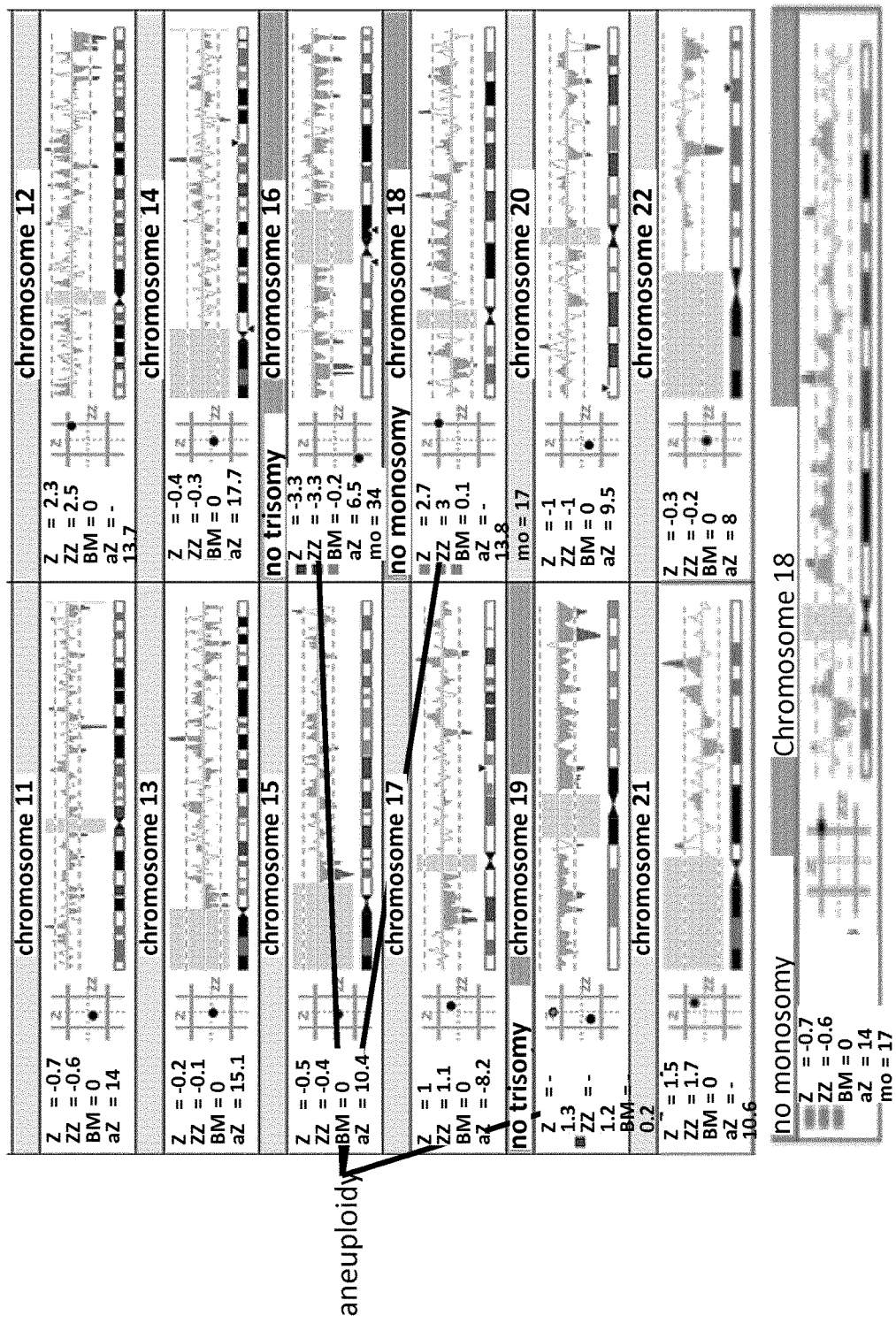
Figure 21:
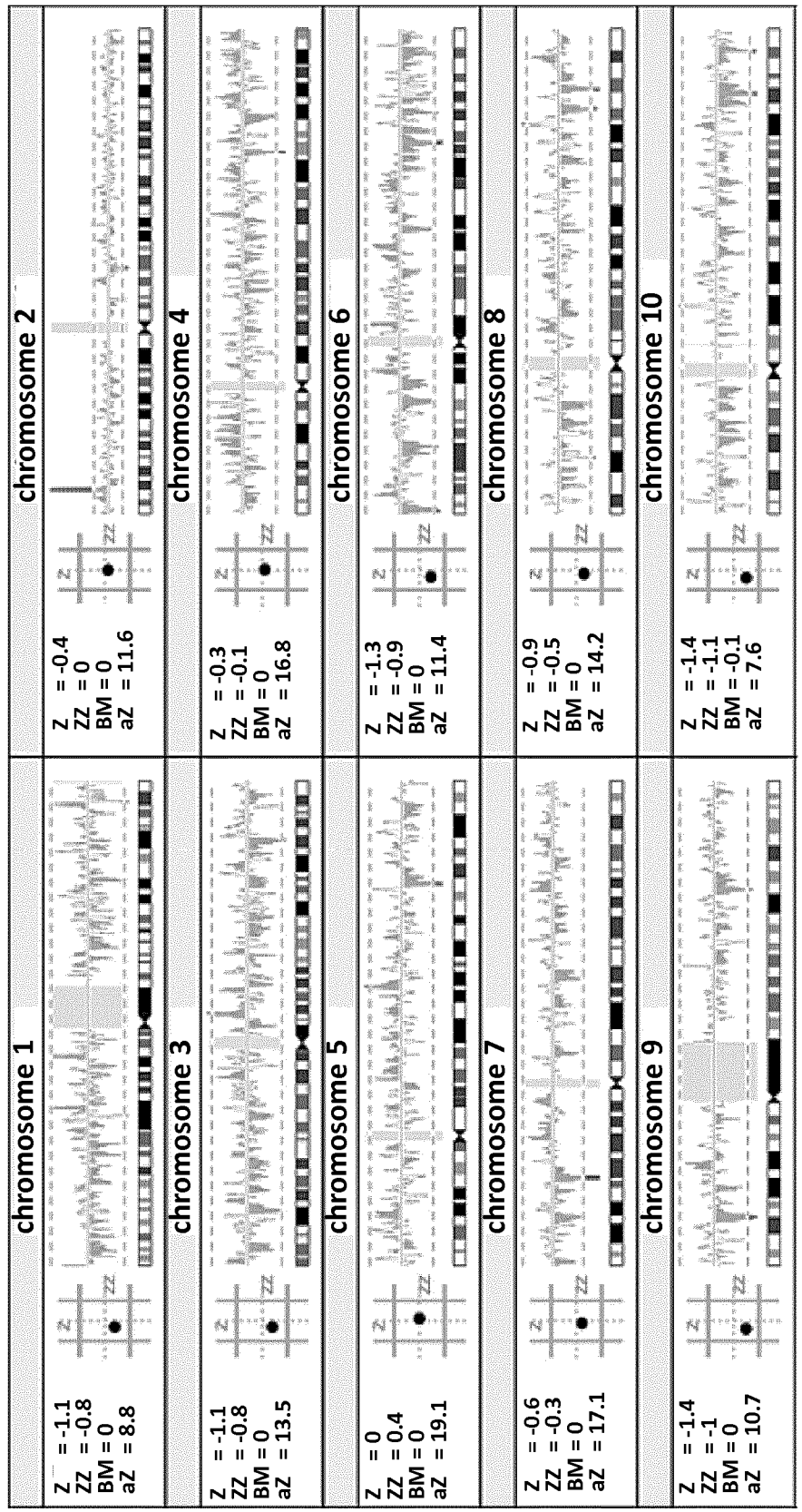
Figure 21:
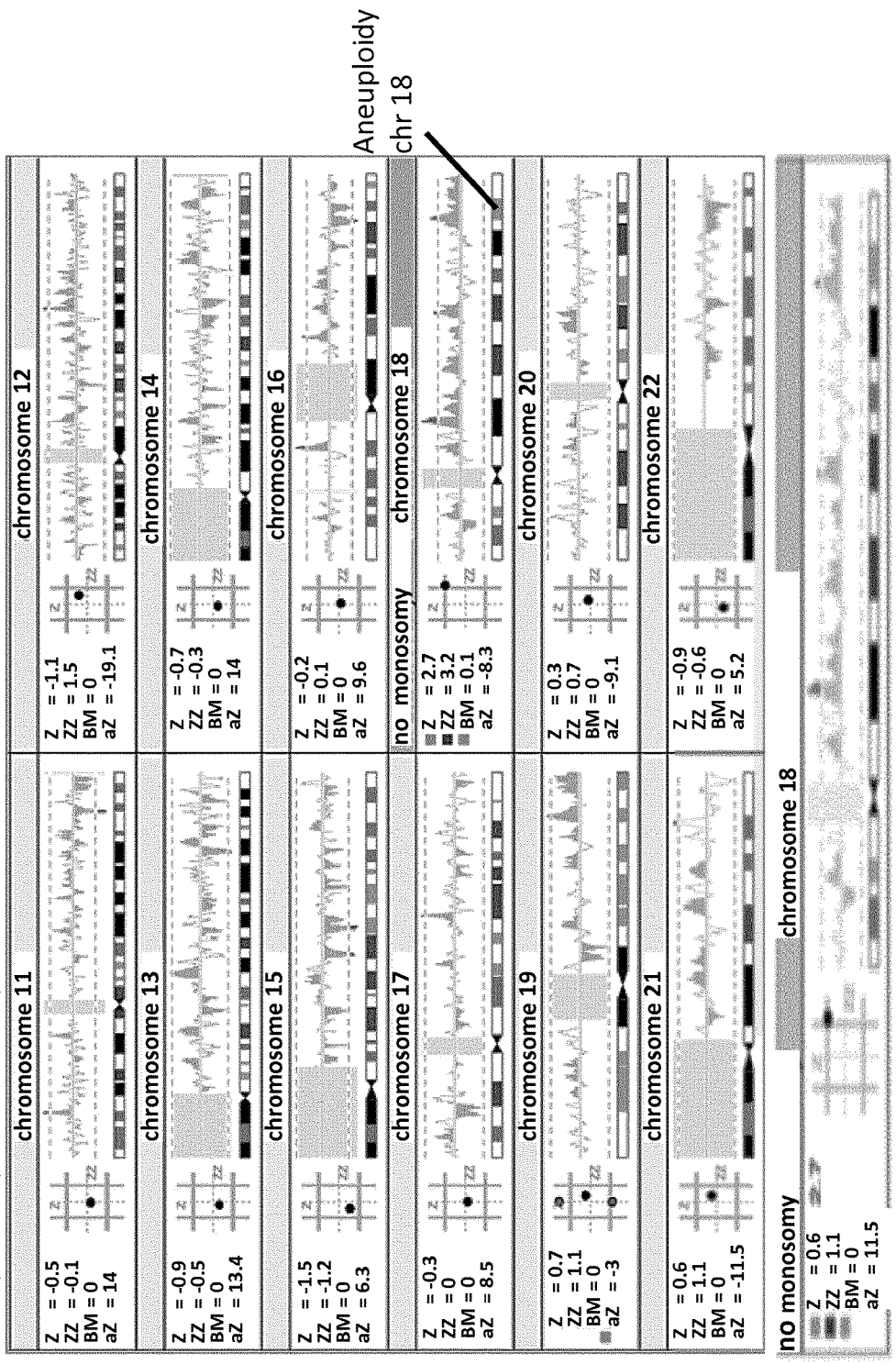

Samples Lupus1 and Lupus2 show a common distorted GipSeq-count-Z-profile when analysed w.r.t. the manually selected initial reference set, cf. left side of FIGS. 20 and 21. Both samples originate from a pregnant patient diagnosed with Lupus erythematosus (Lupus). A similar GipSeq-count-Z-profile has been observed in about 40 other samples, causing them to cluster together.

Figure 19:
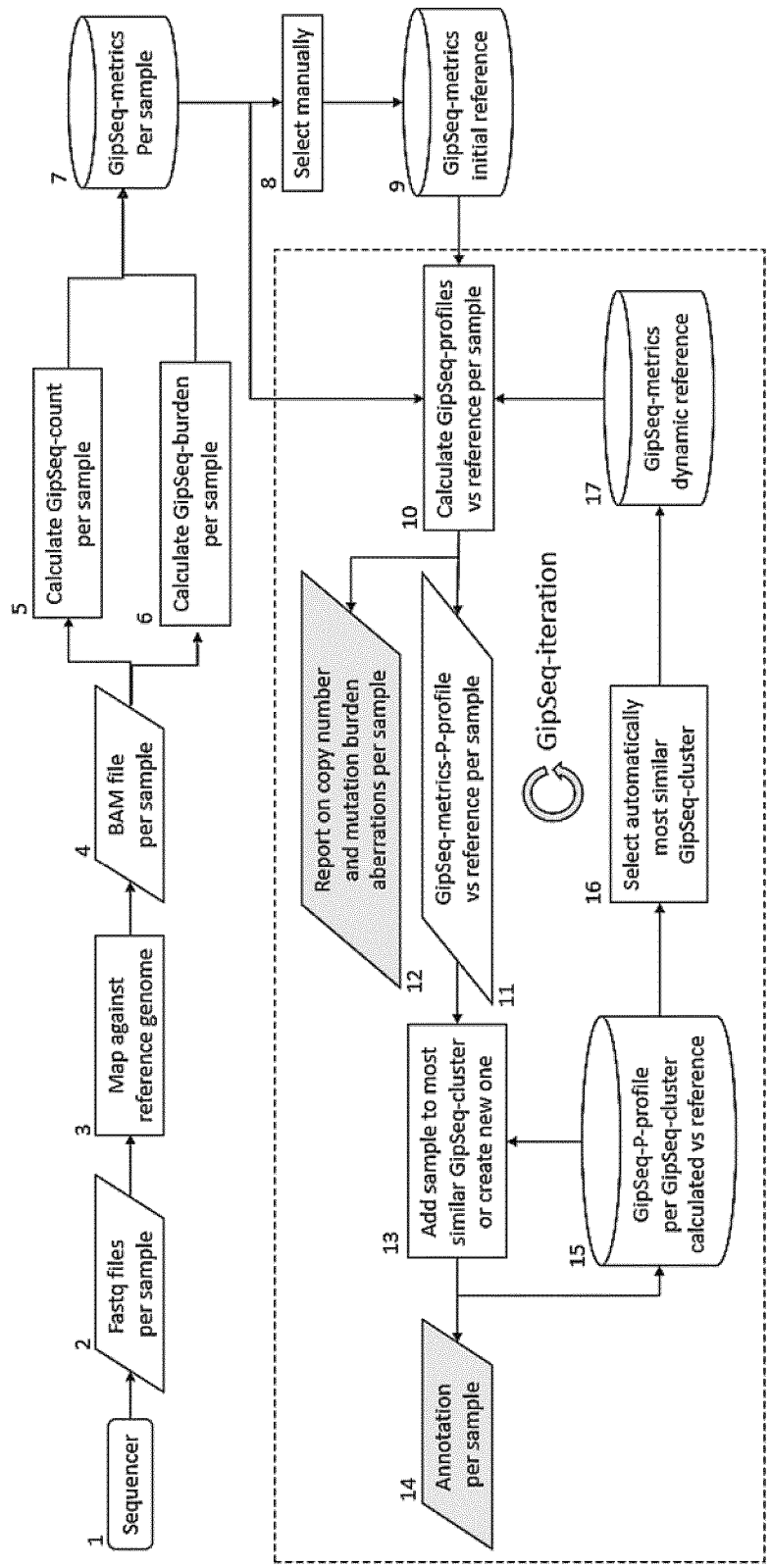
FIG. 19: Overview of the process of iterative refinement of CNA/MBA re-porting (box 12) and sample classification (box 14) with GipSeq.

For these cases, the first iteration of the loop shown in FIG. 19 yields two results:
1. both samples seem to contain multiple (foetal) aneuplodies;
2. they both get the Lupus label, based on their similarity with about 40 previous instances The first outcome is rejected since the presence of multiple foetal aneuploidies is highly unlikely. The state-of-the-art analysis would typically stop here, with the conclusion that the sample is of bad quality and aneuploidies cannot be determined. The second outcome illustrates the first novelty of our approach: both samples are classified as Lupus based on their genome wide imbalance profiles, a diagnosis that was confirmed by the patient profiles.

The right side of FIGS. 20 and 21 illustrates the second advantage of GipSeq. Using the set of about 40 similar cases as a reference set, a second iteration of the FIG. 19-loop is initiated. For sample Lupus1 in FIG. 12 the introduction of this dynamic reference set erases all signs of a (foetal) aneuploidy. The same happens with sample Lupus2 in FIG. 121 except that the chromosome 18 trisomy signal remains. Again, inspection of the patient profiles confirmed this—originally missed—diagnosis.

This example illustrates how the GipSeq-loop outlined in FIG. 19 addresses the complex interaction between sample classification and CNA/MBA detection. Only after highly similar samples Lupus1 and Lupus2 are recognized as members of the Lupus class, the dominating and masking Lupus layer can be "peeled off" by analysing them against a collection of similar cases. As a consequence, the stripped signals start to differ, and the chromosome 18 trisomy in one of them is uncovered.

Example 4—Sample Treatment Identification

FIG. 11 shows the silhouette of the hierarchical clustering tree introduced in the previous section, with the samples prepared using a Hamilton robot (further referred to as Hamilton-samples) highlighted. Notice many of these Hamilton samples cluster towards the right of the tree. This indicates the Hamilton samples differ from the standard reference set in a similar way, to the extent they can be considered a well-defined subpopulation.

FIG. 12 shows the shared GipSeq-profile of the Hamilton samples, i.e., the signature of gains and losses that characterizes this subpopulation.

The GipSeq-profile of the Hamilton samples can now be recalculated using the newly identified Hamilton subpopulation as a reference set. This recursive method to the dynamic composition of an ever more homogeneous reference set could be useful to:
detect more subtle genomic variations in the Hamilton samples that do not raise above the background noise in the context the randomly composed reference set
refine the classification of Hamilton samples into subgroups that only reveal themselves in the context of a less variable reference set For instance, affinity to the tumour profile such as discussed in example 2 could initially be obscured by the dominating Hamilton signature and reveal itself only via dynamic selection of the Hamilton cluster as a reference set.

The invention claimed is:

1. A method for determining a health status of a test individual, the method comprising:
   (a) providing from the test individual a biological sample comprising cell free nucleic acids (cfna);
   (b) determining within at least autosomes, a genome wide distribution of the cfna of the test individual over genomic locations of predetermined regions;
   (c) providing a set of genome wide reference distributions of cfna from a plurality of biological samples of reference individuals, wherein the plurality of reference individuals comprises reference individuals with a disease and healthy reference individuals;
   (d) clustering reference distributions of cfna of a plurality of reference individuals in a test specific reference distribution, wherein the test specific reference distribution is generated by combining the distributions of cfna reference samples which have the highest similarity to the distribution of cfna of the test sample; and (e) determining based on the similarity of the distribution of cfna of the test individual with the identified reference distribution that the test individual has the health status of the reference individual.

2. The method according to claim 1, wherein (b) comprises determining the genome wide distribution within the sex chromosomes of the genome.

3. The method according to claim 1, wherein the test individual is male or is a non-pregnant female.

4. The method according to claim 1, wherein the reference individuals comprise individuals diagnosed with cancer.

5. The method according to claim 1, wherein the set of reference individuals comprises individuals diagnosed with a disorder selected from the group consisting of an autoimmune disease, a cardiovascular disorder, and a metabolic disorder.

6. The method according to claim 1, wherein the size of the disease specific reference distribution is about the square root of the number of reference samples.

7. The method according to claim 1, wherein the set of reference individuals comprises individuals with a genetic disorder comprising a genomic deletion or insertion of between 500 kb and 3 Mb.

8. The method according to claim 7, wherein a genomic deletion or insertion of between 100 kb and 5 Mb is detected.

* * * * *

UNITED STATES PATENT AND TRADEMARK OFFICE
CERTIFICATE OF CORRECTION

| | |
|---|---|
| PATENT NO. | : 11,535,896 B2 |
| APPLICATION NO. | : 16/613991 |
| DATED | : December 27, 2022 |
| INVENTOR(S) | : Luc Dehaspe and Joris Vermeesch |

It is certified that error appears in the above-identified patent and that said Letters Patent is hereby corrected as shown below:

In the Specification

In Column 20, Line(s) 30, delete "FIG." and insert --FIGS.--, therefor.

In Column 20, Line(s) 63, delete "bin 8" and insert --**bin *B***--, therefor.

In Column 26, Line(s) 10, delete "FIG. 18.0" and insert --FIG. 18.C--, therefor.

Signed and Sealed this
Eighteenth Day of April, 2023

Katherine Kelly Vidal
*Director of the United States Patent and Trademark Office*